US008530583B2

(12) United States Patent
Wada et al.

(10) Patent No.: US 8,530,583 B2
(45) Date of Patent: Sep. 10, 2013

(54) THERMO- AND/OR PHOTO-SENSITIVE MATERIAL AND INSULATOR FILM MADE THEREOF

(75) Inventors: Kenji Wada, Shizuoka (JP); Katsuyuki Watanabe, Shizuoka (JP); Keiji Yamamoto, Shizuoka (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/133,827

(22) PCT Filed: Nov. 10, 2009

(86) PCT No.: PCT/JP2009/069106
§ 371 (c)(1),
(2), (4) Date: Jun. 9, 2011

(87) PCT Pub. No.: WO2010/067683
PCT Pub. Date: Jun. 17, 2010

(65) Prior Publication Data
US 2011/0245416 A1    Oct. 6, 2011

(30) Foreign Application Priority Data

Dec. 10, 2008 (JP) .................................. 2008-314856
Feb. 19, 2009 (JP) .................................. 2009-036610

(51) Int. Cl.
*C08F 30/08* (2006.01)

(52) U.S. Cl.
USPC ........ 525/326.5; 525/313; 526/279; 526/281; 522/114

(58) Field of Classification Search
None
See application file for complete search history.

(56) References Cited

U.S. PATENT DOCUMENTS

| 6,911,518 B2 * | 6/2005 | Lichtenhan et al. ............ 528/15 |
| 7,435,989 B2 * | 10/2008 | Nakayama et al. ............ 257/40 |
| 2006/0122351 A1 * | 6/2006 | Laine et al. .................... 528/31 |
| 2007/0085072 A1 | 4/2007 | Masumoto et al. |
| 2008/0214761 A1 | 9/2008 | Morita et al. |
| 2008/0217746 A1 | 9/2008 | Morita et al. |

FOREIGN PATENT DOCUMENTS

| JP | 2000-334881 A | 12/2000 |
| JP | 2003-286347 A | 10/2003 |
| JP | 2005-330414 A | 12/2005 |
| JP | 2007-173472 A | 7/2007 |
| JP | 2007-284652 A | 11/2007 |
| JP | 2008-214454 A | 9/2008 |
| JP | 2008-214487 A | 9/2008 |

OTHER PUBLICATIONS

McClaint et al. MRS Proceedings, vol. 435, 1996.*
Communication, dated May 24, 2012, issued in corresponding EP Application No. 09831789.4, 8 pages.
Baney et al, "Silsesquioxanes," Chemical Reviews, vol. 95, No. 5, Jul. 1, 1995, pp. 1409-1430, XP000535769.
Bent, et al., "Cyclopentadienyl-functionalised polyhedral silsesquioxanes as building blocks for new nanostructured materials," Journal of Organometallic Chemistry, vol. 690, No. 2, Jan. 17, 2005, pp. 463-468, XP004705495.
International Preliminary Report on Patentability and Written Opinion, dated Jul. 14, 2011, issued in corresponding International Application No. PCT/JP2009/069106, 5 pages.
Office Action dated Feb. 12, 2013 in European Application. No. 09 831 789.4.
William C. Herndon et al, Retro-Diels-Alder Reactions. III. Kinetics of the Thermal Decompositions of exo- and endo-Dicyclopentadiene, The Journal of Organic Chemistry, vol. 32, No. 3, Mar. 1, 1967, pp. 526-529.
Office Action dated Jul. 23, 2013 in Japanese Application No. 2009-036610.

* cited by examiner

*Primary Examiner* — Vu A Nguyen
(74) *Attorney, Agent, or Firm* — Sughrue Mion, PLLC

(57) ABSTRACT

A composition for film formation which can form a film suitable for use as an interlayer dielectric in a semiconductor device, etc. and having an appropriate even thickness and can give a film having excellent characteristics including permittivity and Young's modulus; and a dielectric film obtained from the film-forming composition. The composition contains a compound (X) having a functional group which is partly eliminated by heating, irradiation with light, irradiation with radiation, or a combination thereof to generate volatile matter and yield an unsaturated group in the remaining part of the functional group.

8 Claims, No Drawings ptions as dielectric constant and Young's modulus of elasticity from a practical viewpoint, and is disadvantageous in that the surface state of a coating film is deteriorated, and the film thickness considerably decreases during baking.

THERMO- AND/OR PHOTO-SENSITIVE MATERIAL AND INSULATOR FILM MADE THEREOF

CROSS REFERENCE TO RELATED APPLICATIONS

This application is a National Stage of International Application No. PCT/JP2009/069106 filed Nov. 10, 2009, claiming priority based on Japanese Patent Application No. 2008-314856 filed Dec. 10, 2008 and Japanese Patent Application No. 2009-036610 filed Feb. 19, 2009, the contents of all of which are incorporated herein by reference in their entirety.

TECHNICAL FIELD

The present invention relates to compositions, to be more specific, compositions for film formation which, as materials for interlayer insulator films in semiconductor devices and so forth, allow a coating film with an appropriate, uniform thickness to be formed, and are capable of providing an insulator film excellent in such properties as dielectric constant.

BACKGROUND ART

A silica ($SiO_2$) film formed by a vacuum process such as chemical vapor deposition (CVD) generally finds wide application as an interlayer insulator film in a semiconductor device and so forth. Recently, an insulator film of a coating type based on a hydrolysate of tetraalkoxysilane and called a spin-on glass (SOG) film is also used for the purpose of forming a more uniform interlayer insulator film. In addition, an interlayer insulator film of low dielectric constant based on polyorganosiloxane called organic SOG is being developed as the packaging density of semiconductor devices and so forth is increased.

The relative dielectric constant, however, is about 4 even in the case of a CVD-$SiO_2$ film exhibiting a lowest dielectric constant among inorganic films. The SiOF film which, as being a CVD film of low dielectric constant, is being discussed has indeed a relative dielectric constant of about 3.3 to 3.5, but is highly hygroscopic and, accordingly, will be increased in dielectric constant with use.

Under these circumstances, it has been proposed to add a solvent with a high boiling point or a pyrolytic compound to organopolysilixane as an insulator film material excellent in insulating property, heat resistance and durability, so as to form pores in an insulator film and thereby reduce the dielectric constant of the film. A film made porous as above, however, is also reduced in mechanical strength, and its dielectric constant is increased due to the moisture absorbed. Moreover, copper used for wiring may be diffused in the insulator film because the pores formed in the film are communicating with one another.

Also known is an attempt to obtain a film with a low refractive index and a low density by the application of a solution prepared by adding a cage compound of low molecular weight to an organic polymer (see Patent Literature 1). The film which is obtained by the addition of a cage compound monomer, however, is not necessarily satisfactory in such properties as dielectric constant and Young's modulus of elasticity from a practical viewpoint, and is disadvantageous in that the surface state of a coating film is deteriorated, and the film thickness considerably decreases during baking.

CITATION LIST

Patent Literature

Patent Literature 1: JP 2000-334881 A

SUMMARY OF INVENTION

Technical Problems

An object of the present invention is to solve the problems as described above and provide a composition suitably used for an interlayer insulator film in a semiconductor device and so forth, which allows the formation of a film with an appropriate, uniform thickness and the fabrication of an insulator film excellent in such properties as dielectric constant and Young's modulus of elasticity; and an insulator film obtained from such a composition.

Solution to Problems

It has been found that the above object of the present invention is achieved by the following means.

(1) A composition comprising compound (X) having a functional group, wherein the functional group is partially eliminated by heating, irradiation with light, irradiation with radiation, or a combination thereof, so that it generates a volatile component, and yields an unsaturated group in a remaining part.

(2) The composition according to (1), wherein said compound (X) is a compound which has a Diels-Alder adduct moiety produced by Diels-Alder reaction between a conjugated diene structure and a dienophile structure, and generating the conjugated diene structure and the dienophile structure upon retro-Diels-Alder reaction caused by heating, irradiation with light, irradiation with radiation, or a combination thereof, and also has a siloxane structure.

(3) The composition according to (2), wherein said compound (X) is a compound which is produced by Diels-Alder reaction between compound (A) having a dienophile structure and a siloxane structure as well and compound (B) having a conjugated diene structure, and releases the compound (B) having a conjugated diene structure through retro-Diels-Alder reaction caused by heating, irradiation with light, irradiation with radiation, or a combination thereof.

(4) The composition according to (3), wherein said compound (A) having a siloxane structure is compound (I) which has m number of $RSi(O_{0.5})_3$ units (where m is an integer of 8 to 16, and each R is independently a hydrogen atom or a substituent), with the units sharing oxygen atoms therein to link to one another and thereby forming a cage structure, or a polymer of the compound (I).

(5) The composition according to (4), wherein said compound (I) is a compound represented by one out of general formulae (Q-1) through (Q-7):

[Chemical Formula 1]
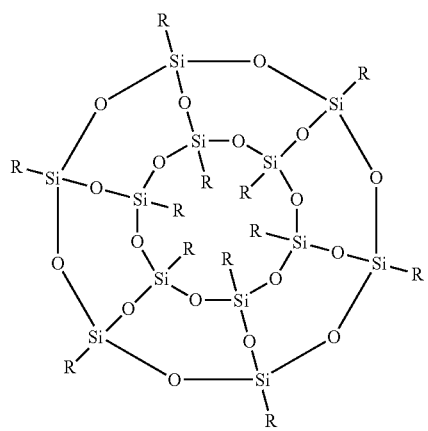
(Q-1)
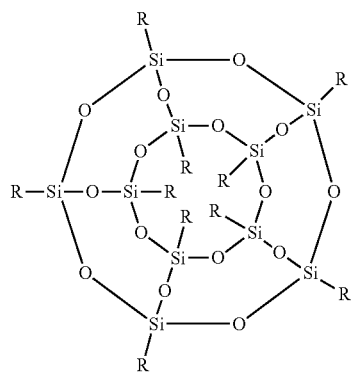
(Q-2)
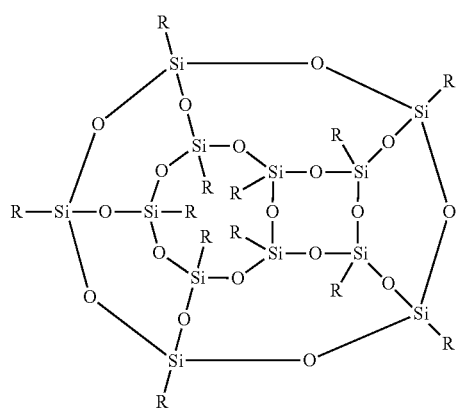
(Q-3)
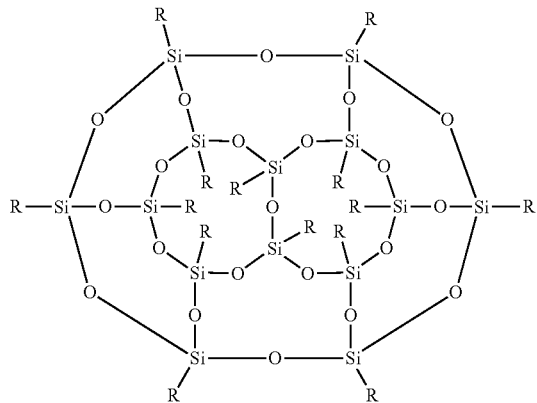
(Q-4)
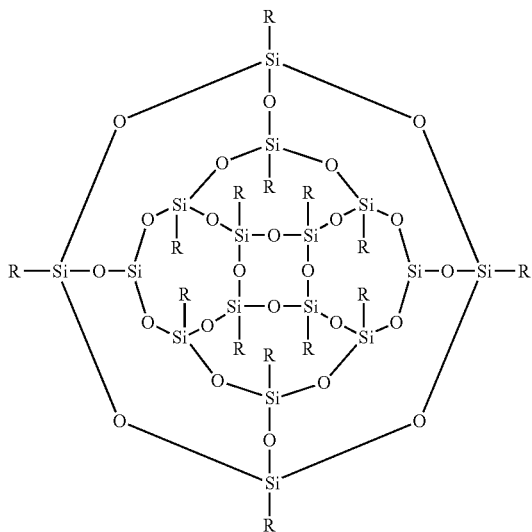
(Q-5)
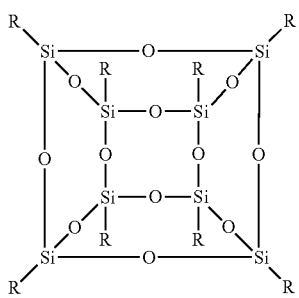
(Q-6)

-continued

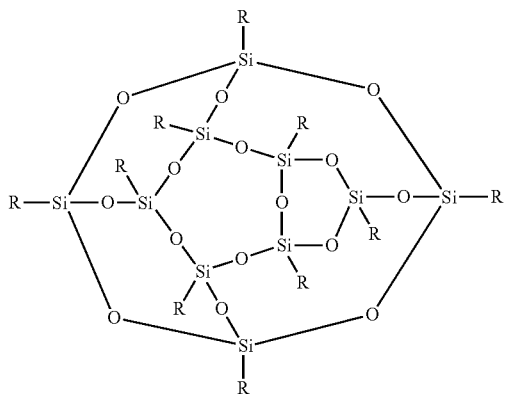
(Q-7)

[in general formulae (Q-1) through (Q-7), each R is independently a hydrogen atom or a substituent; and in each of general formulae (Q-1) through (Q-7), at least one R is an alkenyl group or an alkynyl group].

(6) The composition according to any one of (3) through (5), wherein said compound (B) having a conjugated diene structure is a compound represented by one out of general formulae (B-1) through (B-3):

[Chemical Formula 2]

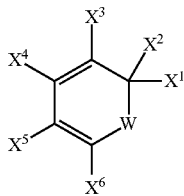
General formula (B-1)

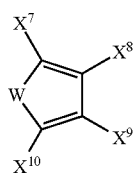
General formula (B-2)

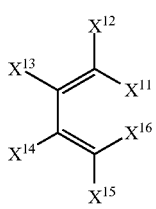
General formula (B-3)

[in general formulae (B-1) through (B-3), $X^1$ to $X^{16}$ are each independently a hydrogen atom or a substituent; and in general formulae (B-1) and (B-2), W is —O—, —C(O)—, —C(O)O—, —S(O)—, —S(O)$_2$—, —C($X^{17}$)($X^{18}$)—, or —N($X^{19}$)—, with $X^{17}$ to $X^{19}$ being each independently a hydrogen atom or a substituent].

(7) The composition according to any one of (3) through (6), wherein said compound (B) having a conjugated diene structure is present in said compound (X) in an addition amount of 5 to 80% by weight based on the total amount of the compound (X).

(8) The composition according to any one of (1) through (7), further comprising a solvent.

(9) The composition according to any one of (1) through (8), which is used for forming an insulator film.

(10) A method of fabricating an insulator film, comprising applying the composition according to any one of (1) through (9) onto a substrate, and curing a film formed of the composition as applied.

(11) An insulator film obtainable by the method according to (10).

(12) An electronic device obtainable using the insulator film according to (11).

(13) A compound having a functional group, wherein the functional group is partially eliminated by heating, irradiation with light, irradiation with radiation, or a combination thereof, so that it generates a volatile component, and yields an unsaturated group in a remaining part.

(14) A resin which has a Diels-Alder adduct moiety produced by Diels-Alder reaction between a conjugated diene structure and a dienophile structure, and generating the conjugated diene structure and the dienophile structure upon retro-Diels-Alder reaction caused by heating, irradiation with light, irradiation with radiation, or a combination thereof, and also has a siloxane structure.

(15) A resin which is produced by Diels-Alder reaction between compound (A) having a dienophile structure and a siloxane structure as well and compound (B) having a conjugated diene structure, and releases the compound (B) having a conjugated diene structure through retro-Diels-Alder reaction caused by heating, irradiation with light, irradiation with radiation, or a combination thereof.

(16) A resin which is produced by Diels-Alder reaction between a compound represented by one out of general formulae (Q-1) through (Q-7):

[Chemical Formula 3]

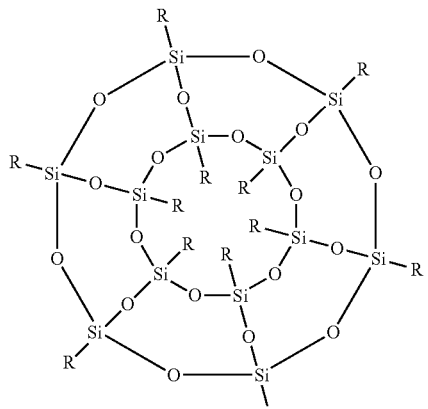
(Q-1)

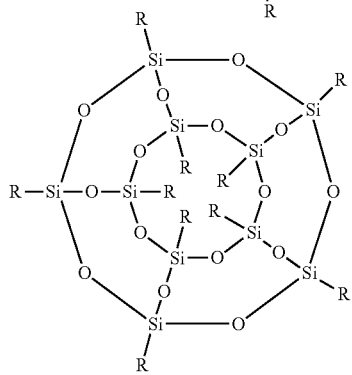
(Q-2)

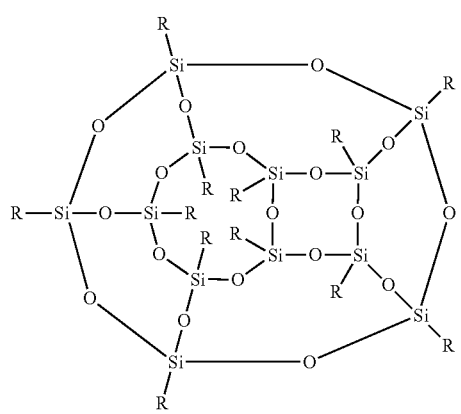
(Q-3)

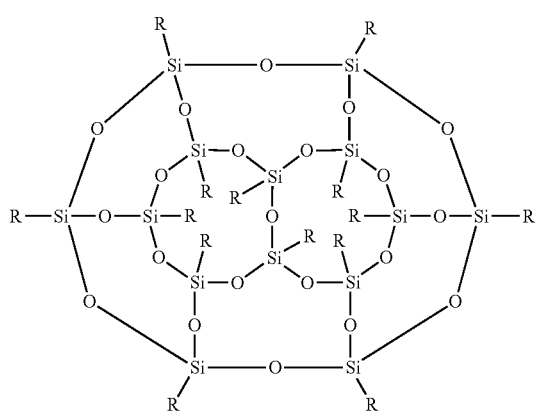
(Q-4)

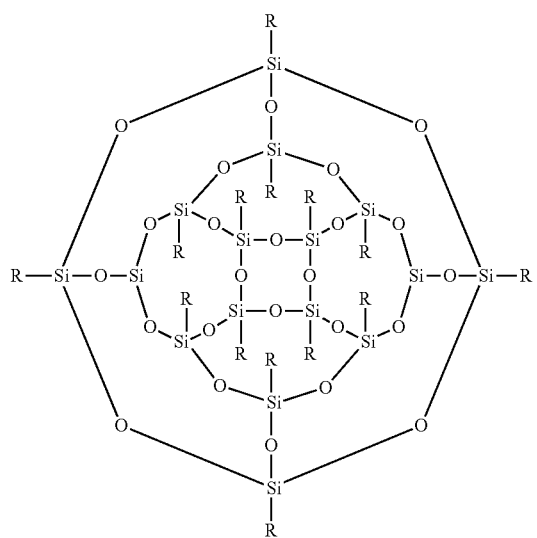
(Q-5)

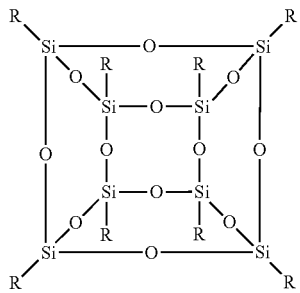
(Q-6)

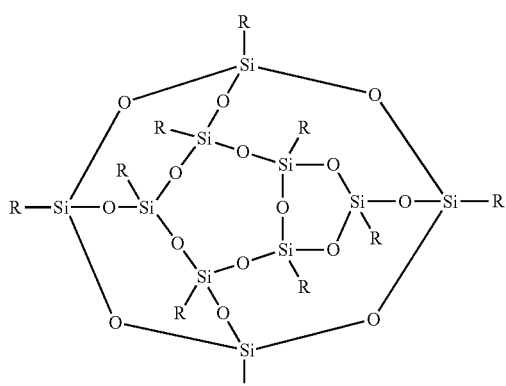
(Q-7)

[in general formulae (Q-1) through (Q-7), each R is independently a hydrogen atom or a substituent; and in each of general formulae (Q-1) through (Q-7), at least one R is an alkenyl group or an alkynyl group] or a polymer thereof and a compound represented by one out of general formulae (B-1) through (B-3):

[Chemical Formula 4]

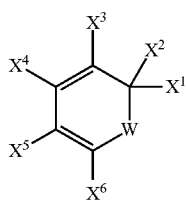
General formula (B-1)

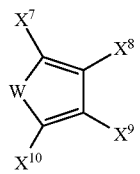
General formula (B-2)

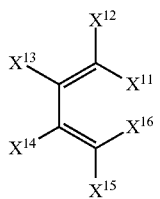
General formula (B-3)

[in general formulae (B-1) through (B-3), $X^1$ to $X^{16}$ are each independently a hydrogen atom or a substituent; and in general formulae (B-1) and (B-2), W is —O—, —C(O)—, —C(O)O—, —S(O)—, —S(O)$_2$—, —C(X$^{17}$) (X$^{18}$)—, or —N(X$^{19}$)—, with X$^{17}$ to X$^{19}$ being each independently a hydrogen atom or a substituent], and releases the compound represented by one out of general formulae (B-1) through (B-3) through retro-Diels-Alder reaction caused by heating, irradiation with light, irradiation with radiation, or a combination thereof.

Advantageous Effects of Invention

According to the present invention, a composition suitably used for an interlayer insulator film in a semiconductor device and so forth, which allows the formation of a film with an appropriate, uniform thickness and the fabrication of an insulator film excellent in such properties as dielectric constant and Young's modulus of elasticity, and an insulator film obtained from such a composition can be provided.

DESCRIPTION OF EMBODIMENTS

In the following, the composition of the present invention and an insulator film obtained from the composition are described in detail.

The composition of the present invention contains compound (X) having the functional group which is partially eliminated by heating, irradiation with light, irradiation with radiation, or a combination thereof to make it generate a volatile component and yield an unsaturated group in a remaining part of the functional group. Compound (X) is initially detailed.

<Compound (X)>

Compound (X) has a functional group, and the functional group is partially eliminated by heating, irradiation with light, irradiation with radiation, or a combination thereof to make it generate a volatile component and yield an unsaturated group in a remaining part of the functional group.

As described later, the composition containing compound (X) is widely applicable. If the composition containing compound (X) is used to fabricate a film, in particular, elimination of the volatile component from the functional group proceeds during heating treatment, or irradiation treatment with a high energy beam such as light or radiation, performed in order to cure a film formed. Generation of the volatile component causes pores to be formed in the film. In addition, an unsaturated group is yielded in a remaining part of the functional group, so that a curing reaction occurs between the remaining groups. As a consequence, a film exhibiting a low dielectric constant, a high refractive index, a high mechanical strength, a high resistance to heat and a high resistance to oxidation stress, with its dielectric constant being stable over a long period of time, can be formed.

Optimal conditions for heating, irradiation with light, irradiation with radiation, or the like vary with the structure of compound (X) used. The volatile component-eliminating reaction generally proceeds in a favorable manner if the conditions for heating treatment or high energy beam irradiation treatment during film fabrication are as described later.

The functional group of compound (X) is partially eliminated by heating, irradiation with light, irradiation with radiation, or a combination thereof to make it generate a volatile component and yield an unsaturated group in a remaining part of the functional group. The functional group is not particularly limited, with its examples including a dithiocarboxylate ester-containing group, a thioester-containing group, an ester-containing group, an azo group-containing group, a carbon-to-carbon double bond-containing group, a sulfonate ester-containing group, a carbamato group-containing group, a carbonato group-containing group, and a silicon atom-containing group.

Specific examples include functional groups (G-1) through (G-7) below, and the Diels-Alder adduct moieties as described later.

[Chemical Formula 5]

(G-1)

(G-2)

(G-3)

(G-4)

(G-5)

(G-6)

(G-7)

In functional groups (G-1) and (G-3), R$^{30}$ is a hydrocarbon group.

Exemplary hydrocarbon groups include a saturated hydrocarbon group (e.g., alkyl group), and an aromatic hydrocarbon group (e.g., benzene group). The symbol "*" denotes the binding site.

In functional group (G-1), X is S, O, Se or Te (preferably S or O). The two Xs in the group (G-1) may or may not be the same.

In functional group (G-1), L is a divalent linking group. Exemplary divalent linking groups include a substituted or unsubstituted alkylene group with a carbon number of 1 to 20 (e.g., methylene group, ethylene group, propylene group, butylene group, isopropylene group), and a substituted or unsubstituted arylene group (e.g., o-phenylene group, m-phenylene group, p-phenylene group, 1,4-naphthylene group).

In functional group (G-2), each Y is independently an alkyl group, an alkenyl group, a silicon atom-containing group, a cycloalkyl group or an aryl group. The Ys may or may not be the same. L is a divalent linking group. Exemplary divalent linking groups include those as mentioned above.

The silicon atom-containing group as represented by Y is defined identically to that represented by R, which is to be described later.

The volatile component generated from the functional group through elimination is not particularly limited but varies with the structure of the functional group. Examples include dithiocarboxylic acid, thioester, thiol, ester, nitrogen molecule, amine, alkane, alkene, alkyne, alcohol, sulfonic acid, silane, silanol, and carbon dioxide.

The unsaturated group as a remaining part of the functional group is not particularly limited as long as it contains a carbon-to-carbon double bond or carbon-to-carbon triple bond. Preferred examples include an alkenyl group (whose carbon number being preferably 1 to 6, more preferably 1 or 2; specifically exemplified by a vinyl group and an allyl group), and an alkynyl group (whose carbon number being preferably 1 to 6, more preferably 1 or 2; specifically exemplified by an ethynyl group).

During the curing of a film, a crosslinking reaction proceeds between the unsaturated groups as above, which allows a film of good mechanical strength.

Compound (X) may be a low molecular-weight compound or a high molecular-weight compound (resin for instance), and is not particularly limited in structure. If compound (X) is to be a high molecular-weight compound, its major skeleton is exemplified by polyimide, polyurethane, polyethylene, polyester, polyphenylene ether, polybenzoxazole, polyarylene ether, a siloxane structure (Si—O bond), a cage structure, a diamondoid structure, and a diamondoid-arylene structure.

Examples of compound (X) with a high resistance to heat include a compound having polyarylene ether, polybenzoxazole or a siloxane structure (Si—O bond), or a polymer thereof; and a compound having a cage structure selected from the group consisting of adamantane, biadamantane, diamantane, triamantane, tetramantane and dodecahedrane, or a polymer thereof. Among others, a compound having a siloxane structure (Si—O bond), or a polymer thereof is preferred.

Compound (X) whose major skeleton is polyarylene ether may be synthesized in reference to JP 2003-520864 A, for instance.

Compound (X) whose major skeleton is polybenzoxazole may be synthesized in reference to WO 2005/019305 utilizing a benzoxazole precursor.

A compound having a siloxane structure refers to a compound having the siloxane structure which is composed of a silicon atom and an oxygen atom, and exhibiting a high resistance to heat. In its favorable form, the compound is a silsesquioxane compound because the latter is low in dielectric properties and good in mechanical properties. A silsesquioxane compound means a compound having at least a silsesquioxane structure. In a silsesquioxane structure, each silicon atom is bound to three oxygen atoms, while each oxygen atom is bound to two silicon atoms (the ratio of the oxygen atom number to the silicon atom number being 1.5) ($Si(O_{0.5})_3$). Exemplary silsesquioxane compounds include ladder-type ones, cage-type ones, incomplete cage-type ones, namely, cage-type ones with lacking parts, and a mixture thereof, with cage-type silsesquioxane compounds (cage silsesquioxanes) being preferred from the viewpoint of the heat resistance and so forth. It should be noted that the term "cage" or "cage-type" as used herein means that the structure in question is such that its cavity is defined by a plurality of rings formed of covalently bound atoms, and points within the cavity cannot leave the cavity without passing through the rings.

The compound which has the functional group as described before and a siloxane structure as well is exemplified by compounds of the following structures, which are each synthesizable in a known manner.

[Chemical Formula 6]

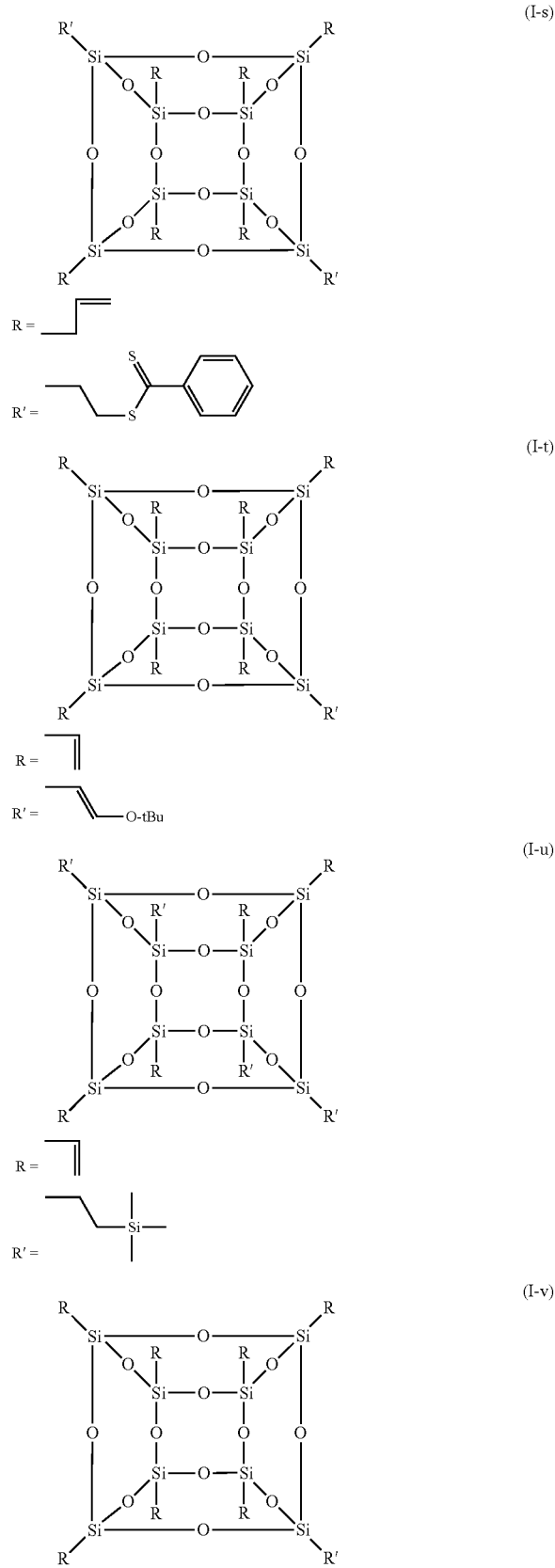

-continued

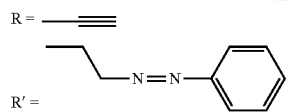

[Chemical Formula 7]

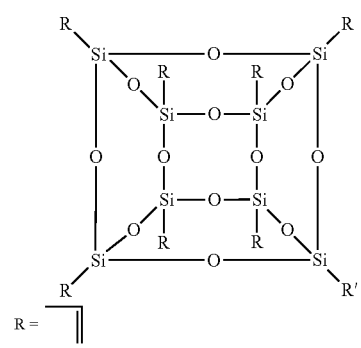
(I-w)

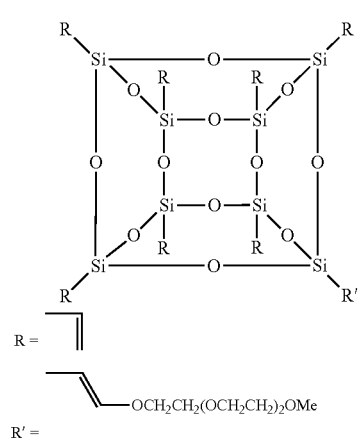
(I-x)

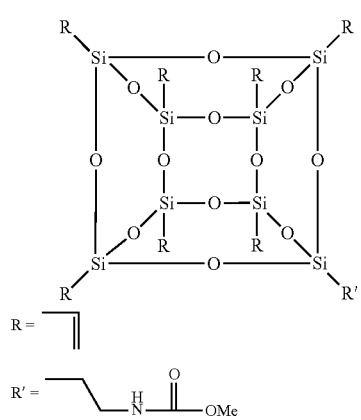
(I-y)

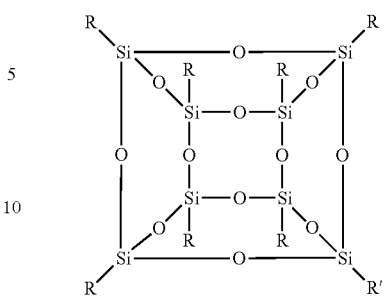
(I-z)

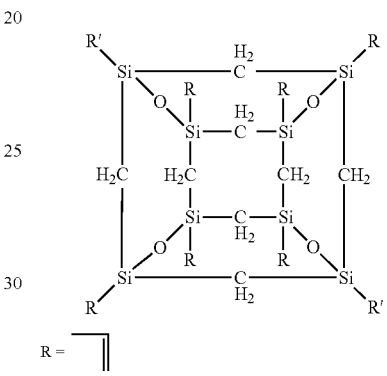
(I-aa)

With respect to the compound having a cage structure as mentioned before, the meaning of "cage" is as defined above. Specific examples of the cage structure include adamantane, biadamantane, diamantane, triamantane, tetramantane and dodecahedrane, with adamantane, biadamantane and diamantane being preferred because of their low dielectric properties and high resistances to heat.

The compound having a cage structure as above is preferably a polymer of a compound having a cage structure containing a polymerizable carbon-to-carbon double bond and/or carbon-to-carbon triple bond. More preferably, the compound having a cage structure is a compound represented by one out of general formulae (H-1) through (H-6), or a polymer thereof.

[Chemical Formula 8]

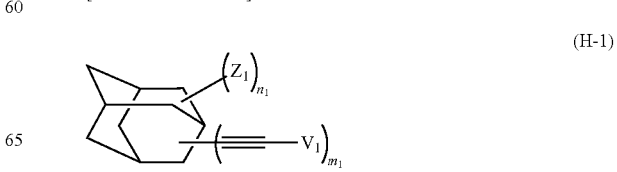
(H-1)

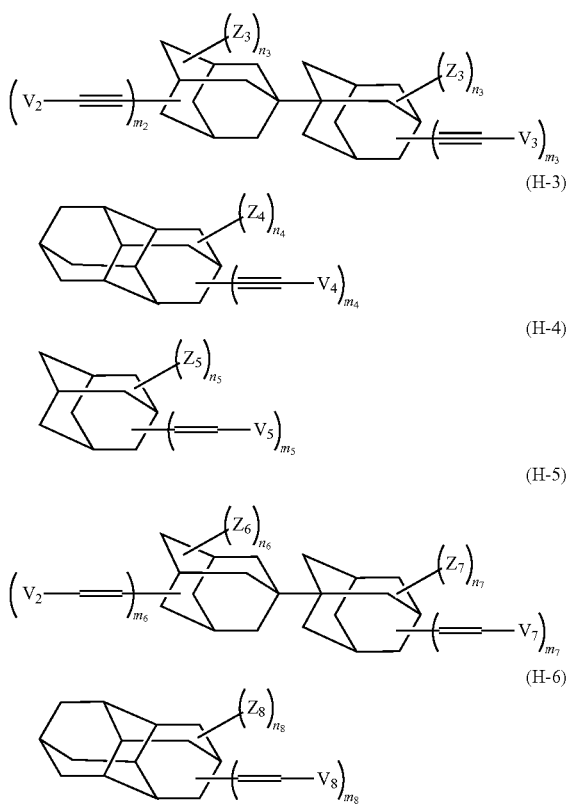

(H-2)

(H-3)

(H-4)

(H-5)

(H-6)

In general formulae (H-1) through (H-6): $V_1$ to $V_8$ are each independently a hydrogen atom, an alkyl group, an alkenyl group, an alkynyl group, an aryl group, a silyl group, an acyl group, an alkoxycarbonyl group, or a carbamoyl group; $Z_1$ to $Z_8$ are each independently a halogen atom, an alkyl group, an aryl group, or a silyl group; $m_1$ and $m_5$ are each independently an integer of 1 to 16 (preferably 1 to 3, more preferably 2); $n_1$ and $n_5$ are each independently an integer of 0 to 15 (preferably 0 or 1); $m_2$, $m_3$, $m_6$ and $m_7$ are each independently an integer of 1 to 15 (preferably 1 to 3, more preferably 2); $n_2$, $n_3$, $n_6$ and $n_7$ are each independently an integer of 0 to 14 (preferably 0 or 1); $m_4$ and $m_8$ are each independently an integer of 1 to 20 (preferably 1 to 3, more preferably 2); as well as $n_4$ and $n_8$ are each independently an integer of 0 to 19 (preferably 0 or 1).

The functional group as described before which yields an unsaturated group in a remaining part may be attached to any site on a compound represented by one out of general formulae (H-1) through (H-6) or a polymer thereof.

A compound represented by one out of general formulae (H-1) through (H-6) is polymerizable in a known manner (by radical polymerization, for instance).

<Compound (Y)>

A suitable embodiment of compound (X) as described above is compound (Y) which has a Diels-Alder adduct moiety produced by Diels-Alder reaction between a conjugated diene structure and a dienophile structure, and generating the conjugated diene structure and the dienophile structure upon retro-Diels-Alder reaction caused by heating, irradiation with light, irradiation with radiation, or a combination thereof, and also has a siloxane structure. Compound (Y) is detailed below.

Compound (Y) is a compound having a Diels-Alder adduct moiety and a siloxane structure as well. In the present invention, a Diels-Alder adduct moiety refers to a moiety having a ring structure formed by Diels-Alder reaction between a conjugated diene structure and a dienophile structure. The moiety generates the conjugated diene structure and the dienophile structure upon retro-Diels-Alder reaction caused by heating, irradiation with light, irradiation with radiation, or a combination thereof.

The composition containing compound (Y) is widely applicable as described later. If the composition containing compound (Y) is used to fabricate a film, in particular, retro-Diels-Alder reaction proceeds during heating treatment, or irradiation treatment with a high energy beam such as light or radiation, performed in order to cure a film formed. Upon the retro-Diels-Alder reaction, the Diels-Alder adduct moiety is dissociated into the conjugated diene structure and the dienophile structure, and either or both of them volatilize to increase the film porosity. In addition, a curing reaction occurs between remaining groups. As a consequence, a film exhibiting a low dielectric constant, a high refractive index, a high mechanical strength, a high resistance to heat and a high resistance to oxidation stress, with its dielectric constant being stable over a long period of time, can be fabricated.

<Conjugated Diene Structure>

The conjugated diene structure to be used for producing a Diels-Alder adduct moiety is not particularly limited, and acyclic and cyclic conjugated diene structures are both available. Preferred examples include the following conjugated diene structures.

[Chemical Formula 9]

(D-1)

(D-2)

(D-3)

(D-4)

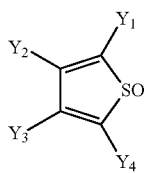 (D-5)

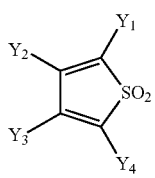 (D-6)

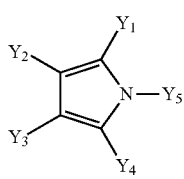 (D-7)

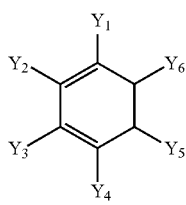 (D-8)

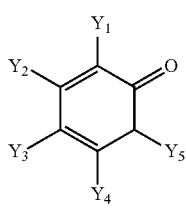 (D-9)

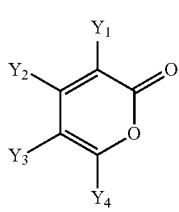 (D-10)

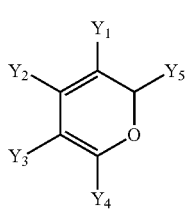 (D-11)

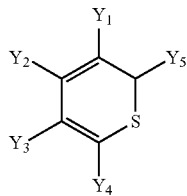 (D-12)

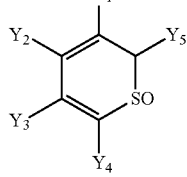 (D-13)

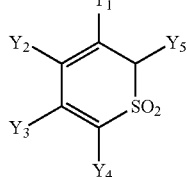 (D-14)

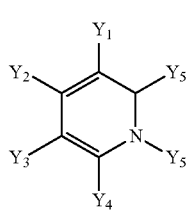 (D-15)

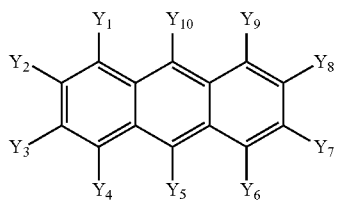 (D-16)

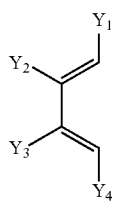 (D-17)

Among others, cyclic conjugated diene structures are preferable because of their high stabilities toward heat and so forth, with skeletons (D-1), (D-2), (D-8), (D-9), (D-10), and (D-11) being particularly preferred.

In skeletons (D-1) through (D-17), $Y_1$ to $Y_{10}$ are each independently a hydrogen atom or a substituent. In this regard, the substituent is defined identically to that in general formulae (F-1) through (F-4) as described later.

<Dienophile Structure>

The dienophile structure to be used for producing a Diels-Alder adduct moiety is not particularly limited as long as it is the unsaturated structure which shows addition reaction with the conjugated diene structure as described above to yield a ring structure, and examples include an alkenyl group with a carbon-to-carbon double bond, and an alkynyl group with a carbon-to-carbon triple bond. Preferred examples include the following dienophile structures, with skeletons (E-1), (E-2), and (E-3) being particularly preferred.

[Chemcial Formula 10]

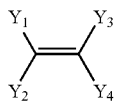
(E-1)

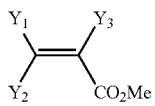
(E-2)

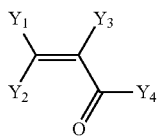
(E-3)

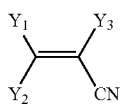
(E-4)

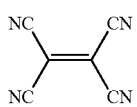
(E-5)

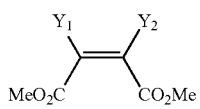
(E-6)

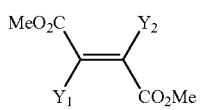
(E-7)

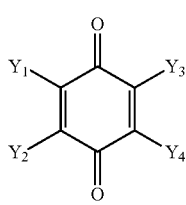
(E-8)

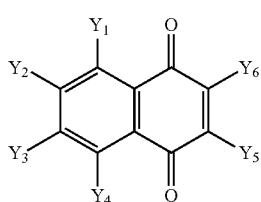
(E-9)

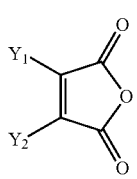
(E-10)

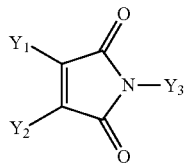
(E-11)

(E-12)

(E-13)

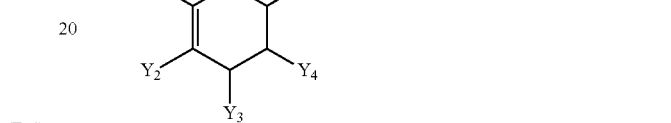
(E-14)

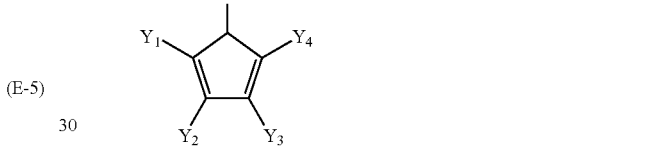
(E-15)

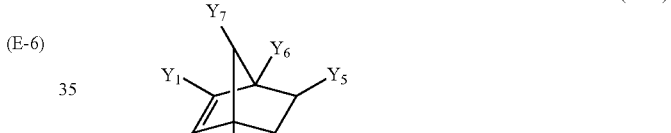
(E-16)

In skeletons (E-1) through (E-16), $Y_1$ to $Y_7$ are each independently a hydrogen atom or a substituent. The substituent is defined identically to that in general formulae (F-1) through (F-4) as described later.

<Diels-Alder Adduct Moiety>

The Diels-Alder adduct moiety in the present invention is the adduct moiety which is obtained by addition reaction between the conjugated diene structure and the dienophile structure as described above, and generates the conjugated diene structure and the dienophile structure upon retro-Diels-Alder reaction caused by heating, irradiation with light, irradiation with radiation, or a combination thereof.

Optimal conditions for heating, irradiation with light, irradiation with radiation, or the like vary with compounds used. Retro-Diels-Alder reaction generally proceeds if the conditions for heating treatment or high energy beam irradiation treatment during film fabrication are as described later.

The Diels-Alder adduct moiety in compound (Y) is not particularly limited in number, and the number is selected as appropriate to the use of interest.

Preferred examples of the Diels-Alder adduct moiety include structures represented by the following general formulae (F-1) through (F-4). By employing such a structure, the control of retro-Diels-Alder reaction will be easier, and the inventive composition will be applied suitably to such uses as insulator film fabrication described later.

[Chemical Formula 11]

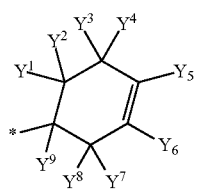

General formula (F-1)

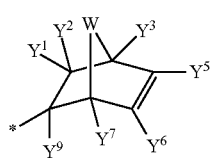

General formula (F-2)

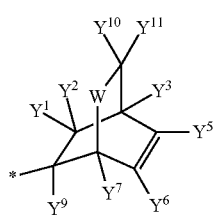

General formula (F-3)

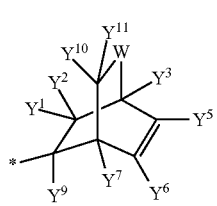

General formula (F-4)

[in general formulae (F-1) through (F-4), $Y^1$ to $Y^{11}$ are each a hydrogen atom or a substituent;
in general formulae (F-2) through (F-4), W is —O—, —C(O)—, —C(O)O—, —S(O)—, —S(O)$_2$—, —C($Y^{12}$)) or —N($Y^{14}$)) with $Y^{12}$ to $Y^{14}$ being each independently a hydrogen atom or a substituent; and in general formulae (F-1) through (F-4), the symbol "*" denotes the site of binding with compound (Y)].

In general formulae (F-1) through (F-4), $Y^1$ to $Y^{11}$ are each a hydrogen atom or a substituent. Exemplary substituents include an alkyl group, a cycloalkyl group, an aryl group, an aralkyl group, an alkenyl group, an alkynyl group, an alkoxy group, a silicon atom-containing group, and a combination thereof. Among others, alkyl, cycloalkyl, aryl, alkoxy, and silicon atom-containing groups are preferable.

The groups as above are defined identically to those represented by R as described later.

In general formulae (F-2) through (F-4), W is —O—, —C(O)—, —C(O)O—, —S(O)—, —S(O)$_2$—, —C($Y^{12}$)($Y^{13}$)—, or —N($Y^{14}$)—. Among others, —O—, —C(O)—, and —C($Y^{12}$)($Y^{13}$)— are preferable.

$Y^{12}$ to $Y^{14}$ are each independently a hydrogen atom or a substituent. The substituents as represented by $Y^{12}$ to $Y^{14}$ are defined identically to those represented by $Y^1$ to $Y^{11}$. Among others, an alkyl group and a cycloalkyl group are preferable.

<Siloxane Structure>

Compound (Y) is a compound having a siloxane structure (Si—O bond), encompassing low molecular-weight compounds and high molecular-weight compounds (resin for instance). Any compound having a siloxane structure will do as long as it does not impair the effects of the present invention. Compound (Y), as having a siloxane structure composed of a silicon atom and an oxygen atom, exhibits a high resistance to heat. The content of the siloxane structure in compound (Y) is preferably 30 to 100% by weight, more preferably 60 to 100% by weight, of the total amount of compound (Y).

In its favorable form, the compound having a siloxane structure is a silsesquioxane compound because the latter is low in dielectric properties and good in mechanical properties. A silsesquioxane compound means a compound having at least a silsesquioxane structure. In a silsesquioxane structure, each silicon atom is bound to three oxygen atoms, while each oxygen atom is bound to two silicon atoms (the ratio of the oxygen atom number to the silicon atom number being 1.5) ($Si(O_{0.5})_3$). Exemplary silsesquioxane compounds include ladder-type ones, cage-type ones, incomplete cage-type ones, namely, cage-type ones with lacking parts, and a mixture thereof, with cage-type silsesquioxane compounds (cage silsesquioxanes) being preferred from the viewpoint of the heat resistance and so forth. The term "cage" as used herein means that the structure in question is such that its cavity is defined by a plurality of rings formed of covalently bound atoms, and points within the cavity cannot leave the cavity without passing through the rings.

A cage silsesquioxane or a polymer thereof is mentioned as a preferred example of the above silsesquioxane compound because of its high resistance to heat.

As more preferred examples, a cage silsesquioxane formed by m number of $RSi(O_{0.5})_3$ units sharing oxygen atoms therein to link to one another, and a polymer having the cage silsesquioxane as its repeating unit may be mentioned. In that case, m is an integer of 8 to 16. The Rs in m units are each independently a hydrogen atom or a substituent, whereupon at least one R is preferably the Diels-Alder adduct moiety.

While m is an integer of 8 to 16, it is preferably 8, 10, 12, 14 or 16 from the viewpoint of reducing the dielectric constant, more preferably 8, 10 or 12 from the viewpoint of the availability, and most preferably 8 or 12 from the viewpoint of the controllability of polymerization.

Specific examples of the substituent R include an alkyl group, a cycloalkyl group, an aryl group, an aralkyl group, an alkenyl group, an alkynyl group, an alkoxy group, a silicon atom-containing group, and a combination thereof, which are preferably of carbon numbers of 1 to 20.

The alkyl group as represented by R may have a substituent, and is preferably the straight-chain or branched-chain alkyl group with a carbon number of 1 to 20 which may have an oxygen atom, sulfur atom or nitrogen atom in the alkyl chain. Specific examples include straight-chain alkyl groups such as methyl group, ethyl group, n-propyl group, n-butyl group, n-pentyl group, n-hexyl group, n-octyl group, n-dodecyl group, n-tetradecyl group and n-octadecyl group; and branched-chain alkyl groups such as isopropyl group, isobutyl group, t-butyl group, neopentyl group and 2-ethylhexyl group.

The cycloalkyl group as represented by R may have a substituent, and is preferably the cycloalkyl group with a carbon number of 3 to 20 which may be polycyclic, and may have an oxygen atom in a ring. Specific examples include cyclopropyl group, cyclopentyl group, cyclohexyl group, norbornyl group, and adamantyl group.

The aryl group as represented by R may have a substituent, and is preferably the aryl group with a carbon number of 6 to 14 which is exemplified by phenyl group and naphthyl group.

The aralkyl group as represented by R may have a substituent, and is preferably the aralkyl group with a carbon number of 7 to 20 which is exemplified by benzyl group, phenethyl group, naphthylmethyl group, and naphthylethyl group.

The alkoxy group as represented by R may have a substituent, and is preferably the alkoxy group with a carbon number of 1 to 20 which is exemplified by methoxy group, ethoxy group, propoxy group, n-butoxy group, penthyloxy group, hexyloxy group, and heptyloxy group.

The silicon atom-containing group as represented by R is not particularly limited as long as it contains a silicon atom, and is preferably a group represented by general formula (2):

*-L$^1$-Si—(R$^{20}$)$_3$      (2).

In general formula (2), the symbol "*" denotes the site of binding with a silicon atom, and L$^1$ is an alkylene group, —O—, —S—, —Si(R$^{21}$)(R$^{22}$)—, —N(R$^{23}$)—, or a combination thereof as a divalent linking group. Preferably, L$^1$ is an alkylene group, —O—, or a combination thereof as a divalent linking group.

A preferred alkylene group has a carbon number of 1 to 12, more preferably of 1 to 6. In the above formula, R$^{21}$, R$^{22}$, R$^{23}$ and R$^{20}$ are each independently an alkyl group, a cycloalkyl group, an aryl group, an aralkyl group, an alkenyl group, or an alkoxy group. The alkyl group, cycloalkyl group, aryl group, aralkyl group, alkenyl group and alkoxy group as represented by R$^{21}$, R$^{22}$, R$^{23}$ and R$^{20}$ are defined identically to those represented by R, with preferred examples including methyl group, ethyl group, butyl group, cyclohexyl group, vinyl group, and ethynyl group. Most preferably, the silicon atom-containing group as represented by R is a silyloxy group (trimethyl silyloxy, triethyl silyloxy, t-butyldimethyl silyloxy).

The alkenyl group as represented by R may be the group which has a double bond at any site on the alkyl, cycloalkyl, aryl, aralkyl, alkoxy, or silicon atom-containing group as above. Its carbon number is preferably 1 to 12, and more preferably 1 to 6. Examples include vinyl group and allyl group, with vinyl group being preferred from the viewpoint of the controllability of polymerization and the mechanical strength.

The alkynyl group as represented by R may be the group which has a triple bond at any site on the alkyl, cycloalkyl, aryl, aralkyl, alkoxy, or silicon atom-containing group as above. Its carbon number is preferably 1 to 12, and more preferably 1 to 6. Ethynyl group is preferred from the viewpoint of the controllability of polymerization and the mechanical strength.

A preferred example of compound (Y) is a silsesquioxane compound having the Diels-Alder adduct moiety as described before. More preferred is a cage silsesquioxane having the Diels-Alder adduct moiety as described before, or a polymer thereof. A cage silsesquioxane having at least one Diels-Alder adduct moiety represented by one out of general formulae (F-1) through (F-4), or a polymer thereof is even more preferable.

Another preferred example of compound (Y) is a silane coupling agent having the Diels-Alder adduct moiety as described before, or a hydrolytic condensate thereof. More preferred is a silane coupling agent represented by general formula (K):

(R$^{40}$)$_{4-n}$—Si—(X)$_n$      (K)

or a hydrolytic condensate thereof.

In general formula (K): R$^{40}$ is a Diels-Alder adduct moiety represented by one out of general formulae (F-1) through (F-4); X is an alkoxy group or a halogen atom (e.g., chlorine atom); and n is an integer of 1 to 3.

A silane coupling agent represented by general formula (K) is hydrolyzable by a conventional method such as heating.

Compound (Y) is not particularly limited in molecular weight, that is to say, may be a low molecular-weight compound or a high molecular-weight compound (resin for instance).

If compound (Y) is to be a high molecular-weight compound, its weight-average molecular weight (M$_w$) is preferably $2.5 \times 10^4$ to $75 \times 10^4$, more preferably $3.5 \times 10^4$ to $35 \times 10^4$, and most preferably $4.5 \times 10^4$ to $25 \times 10^4$.

The number-average molecular weight (M$_n$) of compound (Y) as a high molecular-weight compound is preferably $1.5 \times 10^4$ to $35 \times 10^4$, more preferably $1.5 \times 10^4$ to $20 \times 10^4$, and most preferably $2.5 \times 10^4$ to $15 \times 10^4$.

The Z+1-average molecular weight (M$_{Z+1}$) of compound (Y) as a high molecular-weight compound is preferably $1.5 \times 10^4$ to $65 \times 10^4$, more preferably $2.5 \times 10^4$ to $50 \times 10^4$, and most preferably $3.5 \times 10^4$ to $35 \times 10^4$.

Weight-average molecular weights and number-average molecular weights falling within the above ranges, respectively, allow the improvement in solubility in an organic solvent and filtrability through a filter, and prevent the generation of particles during the storage, leading to the formation of the coating film of low dielectric constant whose surface state is improved.

From the viewpoint of the solubility in an organic solvent, the filtrability through a filter, and the surface state of a coating film, it is preferable that compound (Y) of the present invention contains essentially no components with a molecular weight of 3,000,000 or higher, with an essential absence of components with a molecular weight of 2,000,000 or higher being more preferable, and it is most preferable that the compound contains no components with a molecular weight of 1,000,000 or higher.

Compound (Y) may be quantified from a GPC chart, HPLC chart, NMR spectrum, UV spectrum or IR spectrum for solid components. A copolymer component may optionally be quantified from the monomer charge ratio, or by performing an NMR-spectral, UV-spectral, IR-spectral, or element-compositional measurement after solid components are purified as required.

<Production Process>

The process for producing compound (Y) is not particularly limited, while the following two processes are preferable.

(1) Production of compound (Y) by Diels-Alder reaction between a compound having a dienophile structure and a siloxane structure as well and a compound having a conjugated diene structure.

(2) Production of compound (Y) by Diels-Alder reaction between a compound having a conjugated diene structure and a siloxane structure as well and a compound having a dienophile structure.

Process (1) is more preferable because synthesis is carried out easily, and the produced compound is suitable for the application as described later.

Detailed description is made below on compound (A) having a dienophile structure and a siloxane structure as well and compound (B) having a conjugated diene structure, both used in process (1).

<Compound (A)>

Compound (A) is the compound which has a dienophile structure, and also has a siloxane structure.

A dienophile structure is the unsaturated structure which shows addition reaction with a conjugated diene structure to yield a ring structure, as described before. The dienophile structure of compound (A) is not particularly limited but exemplified by those mentioned before as exemplary dienophile structures. Among others, an alkenyl group and an alkynyl group are preferable.

Compound (A) is a compound having a siloxane structure (Si—O bond), whereupon any siloxane structure will do as long as it does not impair the effects of the present invention. Compound (A) encompasses low molecular-weight compounds and high molecular-weight compounds (resin for instance). The compound having a siloxane structure composed of a silicon atom and an oxygen atom exhibits a high resistance to heat. The content of the siloxane structure in compound (A) is preferably 30 to 100% by weight, more preferably 60 to 100% by weight, of the total amount of compound (A).

Compound (A) is preferably a silsesquioxane compound because the latter is low in dielectric properties and good in mechanical properties. A silsesquioxane compound means a compound having at least a silsesquioxane structure. In a silsesquioxane structure, each silicon atom is bound to three oxygen atoms, while each oxygen atom is bound to two silicon atoms (the ratio of the oxygen atom number to the silicon atom number being 1.5). Exemplary silsesquioxane compounds include ladder-type ones, cage-type ones, incomplete cage-type ones, namely, cage-type ones with lacking parts, and a mixture thereof, with cage-type silsesquioxane compounds being preferred from the viewpoint of the heat resistance, a long-lasting stability, and so forth. The term "cage" as used herein means that the structure in question is such that its cavity is defined by a plurality of rings formed of covalently bound atoms, and points within the cavity cannot leave the cavity without passing through the rings. A silsesquioxane compound having a cage structure is also referred to as a cage-type silsesquioxane compound.

Examples of the cage-type silsesquioxane compound include the compound which has a cage structure formed by m number of $RSi(O_{0.5})_3$ units sharing oxygen atoms therein to link to one another (hereafter also referred to as "compound (I)"), and a polymer having the compound as its repeating unit. The RS in m units are each independently a hydrogen atom or a substituent.

For compound (I), m is an integer of 8 to 16. Preferably, m is 8, 10, 12, 14 or 16 from the viewpoint of reducing the dielectric constant, more preferably 8, 10 or 12 from the viewpoint of the availability, and most preferably 8 or 12 from the viewpoint of the controllability of polymerization.

Preferred examples of the cage structure of compound (I) include compounds represented by general formulae (Q-1) through (Q-7) below. In the formulae, a free valence denotes the site to which R is to be bound. The compound of general formula (Q-6) is most preferable from the viewpoint of the availability, the controllability of polymerization, and the solubility.

[Chemical Formula 12]

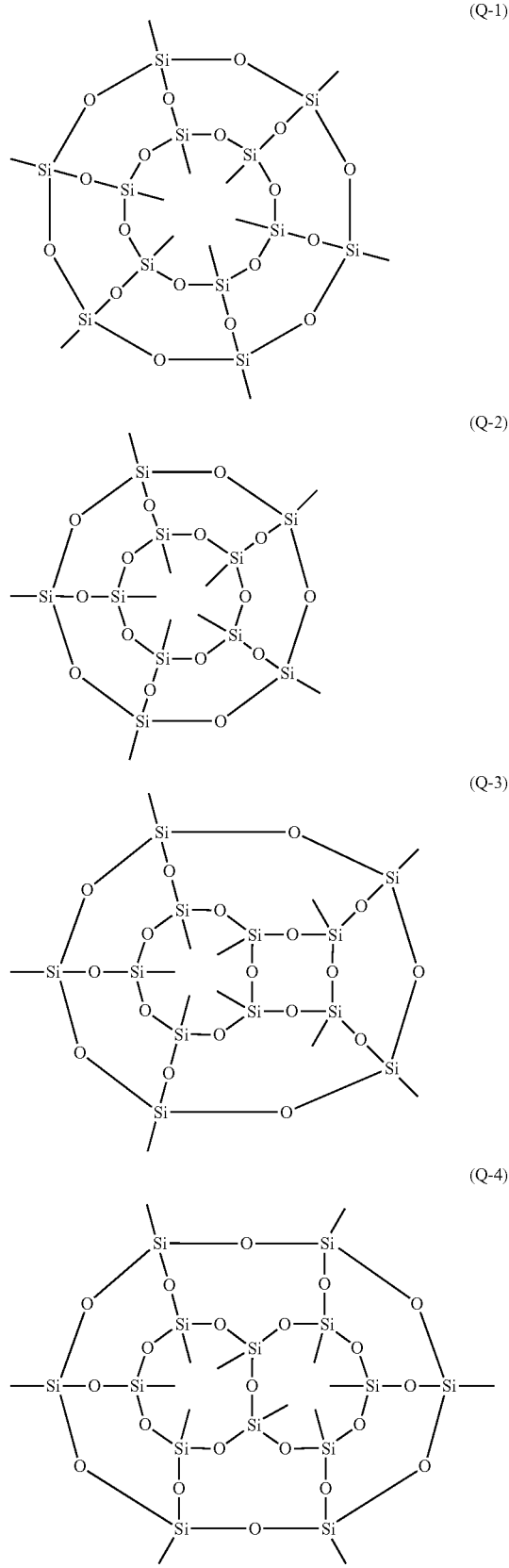

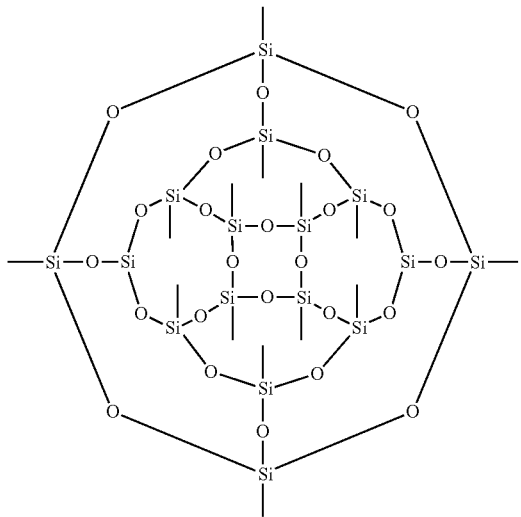

(Q-5)

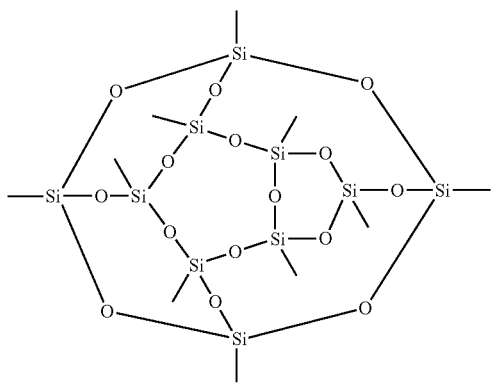

(Q-6)

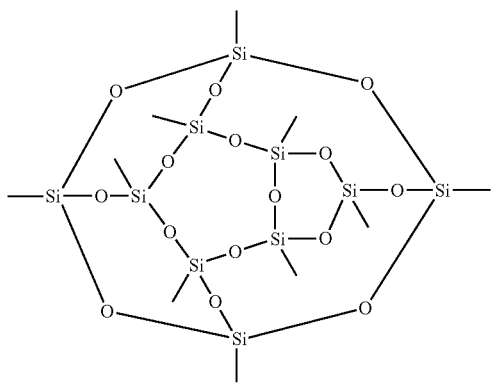

(Q-7)

In compound (I), the Rs of the cage structure are each independently a hydrogen atom or a substituent. The Rs may or may not be the same, whereupon at least one R is an alkenyl group or an alkynyl group.

The substituent as represented by R has the same definition as that detailed above for compound (Y), with specific examples including an alkyl group, a cycloalkyl group, an aryl group, an aralkyl group, an alkenyl group, an alkynyl group, an alkoxy group, a silicon atom-containing group, and a combination thereof, which are preferably of carbon numbers of 1 to 20.

Out of the Rs as above, at least one is an alkenyl group or an alkynyl group. Preferably, not less than two Rs, more preferably not less than three, and even more preferably all the Rs are each an alkenyl group or an alkynyl group. If a plurality of alkenyl or alkynyl groups are present, the retro-Diels-Alder reaction during the curing of a film causes the alkenyl or alkynyl groups as dienophiles to be generated in the film, and crosslinking reaction (curing reaction) proceeds through the dienophiles. As a consequence, the film is improved in mechanical strength.

Specific examples of the cage-type silsesquioxane compound as compound (I) include the following compounds, although the present invention is in no way limited thereto.

[Chemical Formula 13]

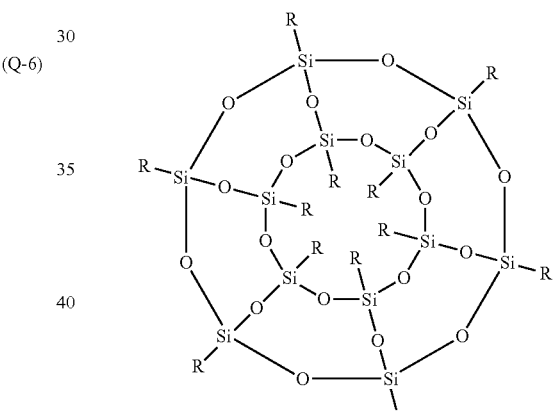

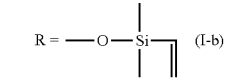

(I-a)

(I-b)

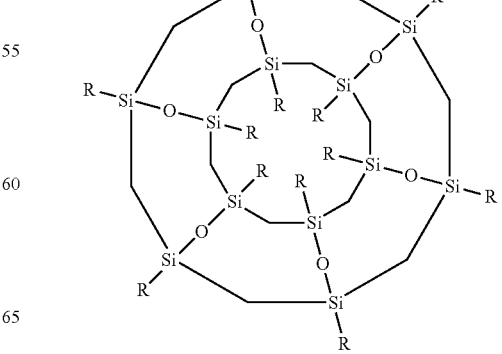

(I-c)

-continued
R = 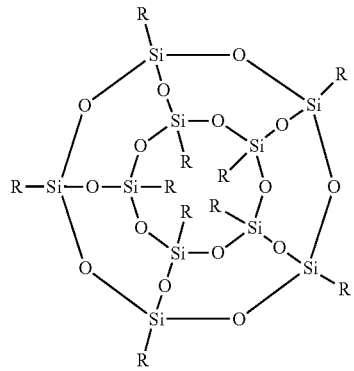
(I-d)
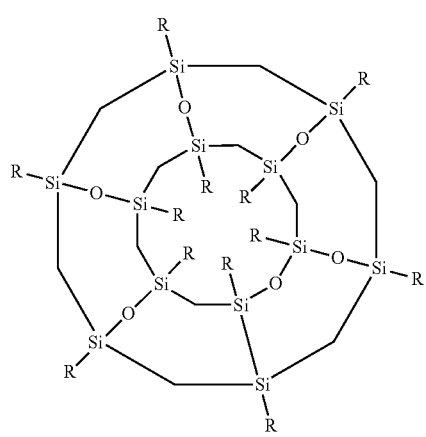
R = 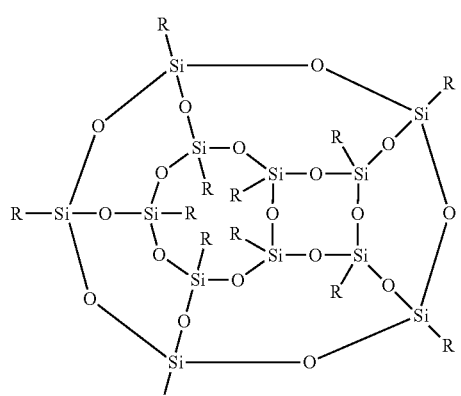
[Chemical Formula 14]
(I-g)
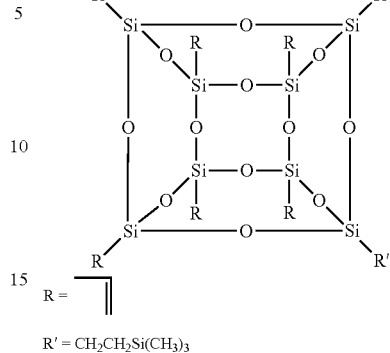
R = 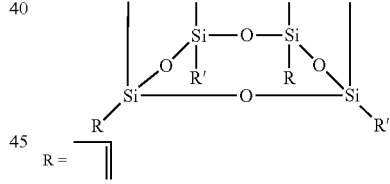
R′ = CH₂CH₂Si(CH₃)₃
(I-h)
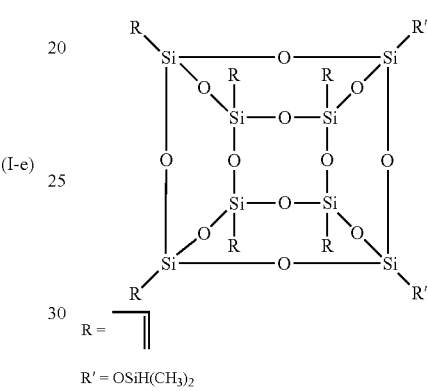
R = 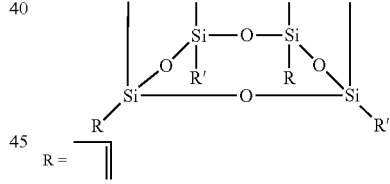
R′ = OSiH(CH₃)₂
(I-i)
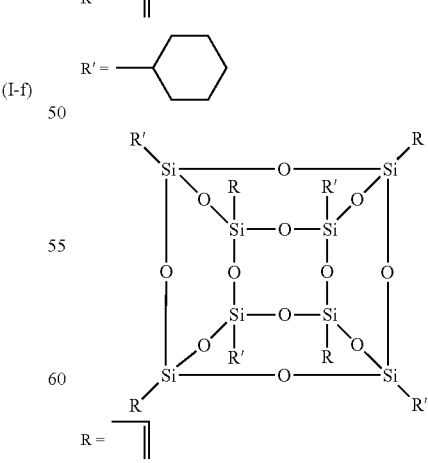
R = 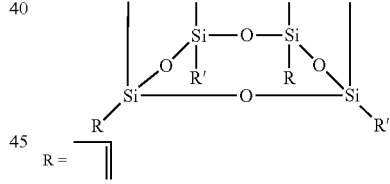
R′ = cyclohexyl
(I-j)
R = 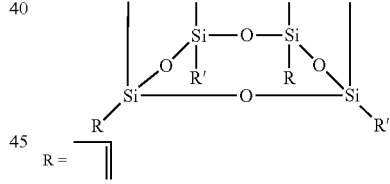
R′ = phenyl

[Chemical Formula 15]

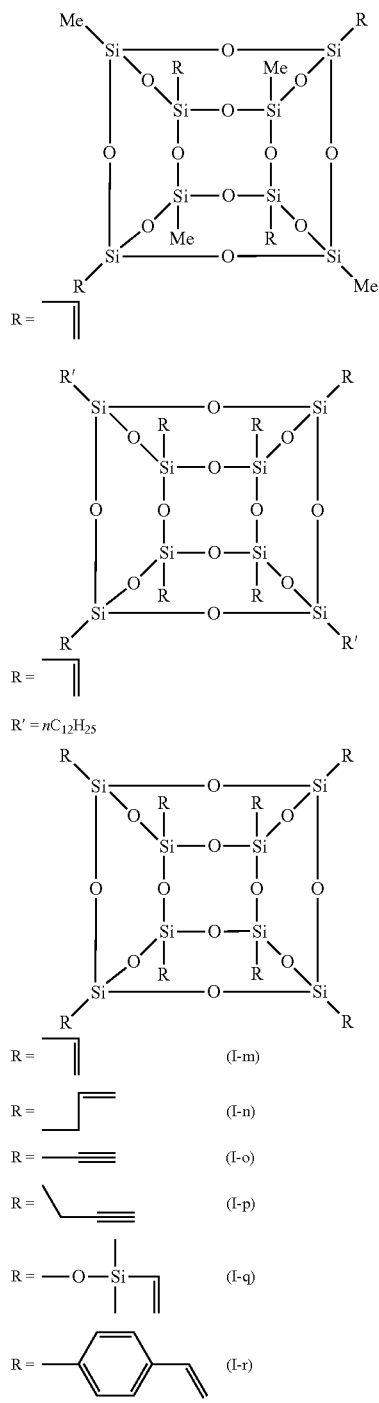

Compound (I) is commercially available from Sigma-Aldrich Corp. or Hybrid Plastics, Inc. The compound may also be synthesized by a known method described in: Polymers, 20, 67-85, 2008; Journal of Inorganic and Organometallic Polymers, 11(3), 123-154, 2001; Journal of Organometallic Chemistry, 542, 141-183, 1997; Journal of Macromolecular Science. A. Chemistry, 44(7), 659-664, 2007; Chem. Rev., 95, 1409-1430, 1995; Journal of Inorganic and Organometallic Polymers, 11(3), 155-164, 2001; Dalton Transactions, 36-39, 2008; Macromolecules, 37(23), 8517-8522, 2004; Chem. Mater., 8, 1250-1259, 1996.

It is also preferable that R in compound (I) of the present invention is a group represented by general formula (II). The group of general formula (II) may be synthesized by reacting a compound represented by general formula (III) with a compound represented by general formula (IV).

$(R^1)_3-Si-O-$ (II)

$[MO-Si(O_{0.5})_3]_m$ (III)

$(R^1)_3-Si-Cl$ (IV)

The compound represented by general formula (III) may be synthesized by the method described in Angew. Chem. Int. Ed. Engl., 1997, 36, No. 7, 743-745.

In the above formulae, $R^1$s are each independently a substituent, with specific examples including an alkyl group, an aryl group, vinyl group, and ethynyl group. The definitions of m and $R^1$ are identical to those of m and R for compound (I). M is a metal atom (e.g., Na, K, Cu, Ni, Mn) or an onium cation (e.g., tetramethyl ammonium). If M is a polyvalent metal atom, a plurality of $-O-Si(O_{0.5})_3$ moieties are to be bound to the polyvalent metal atom M.

The reaction between a compound of general formula (III) and a compound of general formula (IV) is generally conducted at 0 to 180° C. for 10 minutes to 20 hours by, for instance, adding the compounds of general formulae (III) and (IV) to a solvent, with the number of moles of the compound of general formula (IV) being 1 to 100 times as high as the number of Si—OM groups in the compound of general formula (III), and agitating the resultant mixture.

Preferred solvents are organic ones, such as toluene, hexane, and tetrahydrofuran (THF).

A base such as triethyl amine and pyridine may be added to the reaction mixture of the compounds of general formulae (III) and (IV).

Compounds represented by general formulae (Q-8) and (Q-9) are also preferred examples of compound (A).

[Chemical Formula 16]

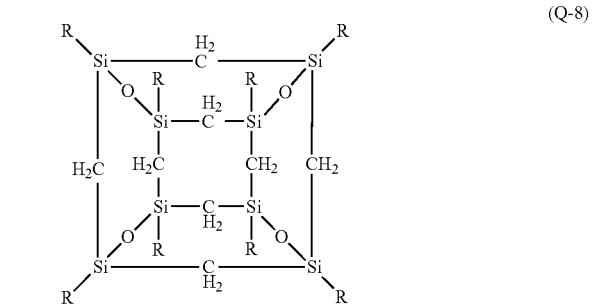
(Q-8)

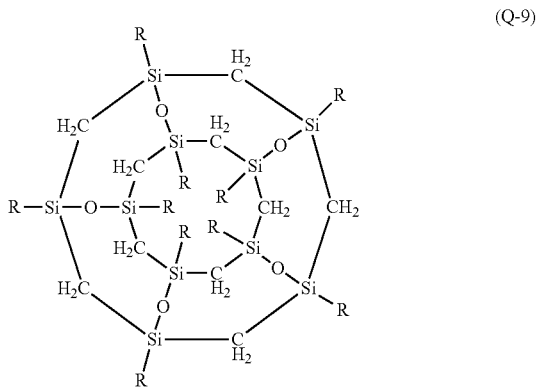
(Q-9)

In general formulae (Q-8) and (Q-9), Rs are each independently a hydrogen atom or a substituent. The Rs in each formula may or may not be the same, whereupon at least one R is an alkenyl group or an alkynyl group. The substituent R is defined identically to the substituent R in compound (I) as described above.

<Polymer>

Preferred examples of compound (A) having a siloxane structure include a polymer having compound (I) as its repeating unit, and examples of such a polymer may include polymers of different compounds (I). In that case, a copolymer of different compounds (I), and a mixture of homopolymers are both included. If the composition of the present invention contains a copolymer of different compounds (I), the copolymer is preferably prepared as a mixture of two or more out of compounds (I) for which m is 8, 10 and 12, respectively.

Compound (A) having a siloxane structure may also be compound (I) copolymerized with another compound. In that case, a compound having a plurality of polymerizable unsaturated carbon-to-carbon bonds, or SiH groups is suitably used. Suitable compounds are exemplified by vinylsilanes, vinylsiloxanes, phenylacetylenes, vinyl adamantanes, and $[(HSiO_{0.5})_3]_8$.

Preferably, compound (I)-derived components comprise not less than 50% by weight, more preferably not less than 70% by weight, of the copolymer.

During the preparation of a polymer having compound (I) as its repeating unit, unreacted compound (I) preferably comprises not more than 15% by weight, more preferably not more than 10% by weight, and most preferably not more than 7% by weight of the total solid components. As a result, the surface state of a coating film can be improved. The term "total solid components" as used herein means the total of the compound (I) polymer and unreacted components.

The weight-average molecular weight ($M_w$) of compound (A) having a siloxane structure is preferably $2.0 \times 10^4$ to $70 \times 10^4$, more preferably $3.0 \times 10^4$ to $30 \times 10^4$, and most preferably $4.0 \times 10^4$ to $20 \times 10^4$, with the compound (I) monomer being left out of account.

The number-average molecular weight ($M_n$) of compound (A) having a siloxane structure is preferably $1.0 \times 10^4$ to $30 \times 10^4$, more preferably $1.0 \times 10^4$ to $15 \times 10^4$, and most preferably $2.0 \times 10^4$ to $10 \times 10^4$, with the compound (I) monomer being left out of account.

The Z+1-average molecular weight ($M_{Z+1}$) of compound (A) having a siloxane structure is preferably $1.0 \times 10^4$ to $60 \times 10^4$, more preferably $2.0 \times 10^4$ to $45 \times 10^4$, and most preferably $3.0 \times 10^4$ to $30 \times 10^4$, with the compound (I) monomer being left out of account.

Weight-average molecular weights and number-average molecular weights falling within the above ranges, respectively, allow the improvement in solubility in an organic solvent and filtrability through a filter, leading to the formation of the coating film of low dielectric constant whose surface state is improved.

From the viewpoint of the solubility in an organic solvent and the filtrability through a filter, it is preferable that the polymer as above contains essentially no component with a molecular weight of 3,000,000 or higher, with an essential absence of a component with a molecular weight of 2,000,000 or higher being more preferable, and it is most preferable that the polymer contains no component with a molecular weight of 1,000,000 or higher.

The polymer of compound (I) preferably has compound (I)-derived alkenyl and alkynyl groups remaining therein as unreacted, whereupon it is preferable that 10 to 90% by mole, more preferably 20 to 80% by mole, and most preferably 30 to 70% by mole of the compound (I)-derived alkenyl and alkynyl groups remain in the polymer as unreacted. If the rate of unreacted alkenyl and alkynyl groups falls within the above range, the curability and the mechanical strength of a film obtained is improved.

The polymer of compound (I) may have a polymerization initiator, an additive, or a solvent for polymerization bound thereto in an amount of 0.1 to 40% by weight on the total amount of the polymer. The amount of such an auxiliary agent is preferably 0.1 to 20% by weight, more preferably 0.1 to 10% by weight, and most preferably 0.1 to 5% by weight on the total amount of the polymer.

Auxiliary agents may be quantified from an NMR spectrum of a composition.

The polymer of compound (I) may be prepared by a method utilizing polymerization reaction between unsaturated carbon-to-carbon bonds in compound (I), hydrosilylation reaction, or sol-gel reaction in the presence of an acid or base catalyst.

The polymerization reaction between unsaturated carbon-to-carbon bonds in compound (I) is not particularly limited but exemplified by radical polymerization, cation polymerization, anion polymerization, ring opening polymerization, polycondensation, addition polymerization, addition condensation, and transition metal-catalyzed polymerization.

Hydrosilylation reaction may be conducted by dissolving the compound of the present invention and, additionally, a compound containing two or more SiH groups in the molecule (e.g., bis(dimethylsilyl)ethane, 1,1,3,3-tetramethyl disiloxane) in an organic solvent (e.g., toluene, xylene), adding a catalyst (e.g., platinum(0)-1,3-divinyl-1,1,3,3-tetramethyl disiloxane complex), and heating the resultant mixture at 20 to 200° C.

Sol-gel reaction may be conducted by following such a process as described in "Application of Sol-Gel Processing to Nanotechnology" (CMC Publishing Co., Ltd., 2005) or "New Development of Application in Sol-Gel Processing" (CMC Publishing Co., Ltd., 2008).

Preferably, the above polymer is prepared by polymerization reaction between unsaturated carbon-to-carbon bonds in compound (I), and the polymerization reaction is most preferably of a radical polymerization type. Synthesis may be carried out by the mixture polymerization method in which compound (I) and an initiator are dissolved in a solvent, and the resultant solution is heated so as to achieve polymerization; the falling-drop polymerization method in which compound (I) is dissolved in a solvent, and, to the solution being heated, an initiator solution is added dropwise for one to ten hours (continuous addition method); or the batch polymerization method in which an initiator is added in portions (divided addition method). The divided addition method and the continuous addition method are preferable because the film strength and the molecular weight-reproducing property are further improved with them.

The temperature of the polymerization reaction in the present invention is generally 0 to 200° C., while preferably 40 to 170° C., and more preferably 80 to 160° C.

The reaction is preferably conducted in an inert atmosphere (e.g., nitrogen gas, argon gas) in order to prevent inactivation of the polymerization initiator by oxygen. The oxygen concentration during the reaction is preferably 100 ppm or less, more preferably 50 ppm or less, and even more preferably 20 ppm or less.

The concentration of compound (I) in the polymerization reaction solution is preferably 30% by weight or lower, more preferably 20% by weight or lower, even more preferably 15% by weight or lower, and most preferably 10% by weight or lower based on the total weight of the reaction solution. Compound (I) concentrations falling within the above range can prevent generation of impurities such as gelatinized components.

Any solvent is usable in the above polymerization reaction as long as it makes compound (I) dissolved at a required concentration and, at the same time, does not affect adversely the properties of a film formed from the obtained polymer. Hereafter, an ester-based solvent refers to a solvent containing an ester group in the molecule, and so forth.

Examples of the solvent which may be used include water; alcohol-based solvents such as methanol, ethanol, propanol, and butanol; ketone-based solvents such as acetone, methyl ethyl ketone, methyl isobutyl ketone, cyclohexane, and acetophenone; ester-based solvents such as methyl acetate, ethyl acetate, propyl acetate, isopropyl acetate, butyl acetate, pentyl acetate, hexyl acetate, methyl propionate, ethyl propionate, propylene glycol monomethyl ether acetate, propylene glycol monobutyl ether acetate, γ-butyrolactone, and methyl benzoate; ether-based solvents such as 1,4-dioxane, diisopropyl ether, dibutyl ether, anisole, tetrohydrofuran, and diphenyl ether; aromatic hydrocarbon-based solvents such as toluene, xylene, mesitylene, 1,2,4,5-tetramethylbenzene, pentamethylbenzene, isopropylbenzene, 1,4-diisopropylbenzene, t-butylbenzene, 1,4-di-t-butylbenzene, 1,3,5-triethylbenzene, 1,3,5-tri-t-butylbenzene, 4-t-butyl-orthoxylene, 1-methylnaphthalene, and 1,3,5-triisopropylbenzene; amide-based solvents such as N-methylpyrrolidinone and dimethyl acetamide; halogen-based solvents such as carbon tetrachloride, dichloromethane, chloroform, 1,2-dichloroethane, chlorobenzene, 1,2-dichlorobenzene, chlorobenzene, and 1,2,4-trichlorobenzene; and aliphatic hydrocarbon-based solvents such as hexane, heptane, octane, and cyclohexane.

Among the above, ester-based solvents, ether-based solvents, and aromatic hydrocarbon-based solvents are preferable. To be more specific, ethyl acetate, propyl acetate, isopropyl acetate, butyl acetate, pentyl acetate, hexyl acetate, methyl propyonate, propylene glycol monomethyl ether acetate, tetrahydrofuran, diphenyl ether, anisole, toluene, xylene, mesitylene, and t-butylbenzene are preferable, with ethyl acetate, butyl acetate, diphenyl ether, anisole, mesitylene, and t-butylbenzene being particularly preferred. These solvents may be used separately, or as a mixture of two or more out of them.

For the purpose of heating the reaction solution to a temperature required for the decomposition of the polymerization initiator during the reaction, it is preferable that the solvent has a boiling point of not less than 65° C.

The polymerization reaction of compound (I) is preferably conducted in the presence of a nonmetallic polymerization initiator. For instance, polymerization may be achieved in the presence of the polymerization initiator which exhibits its activity by generating such free radicals as carbon radicals or oxygen radicals when heated.

Organic peroxides or organic azo compounds are particularly suitable for the use as a polymerization initiator.

Examples of the organic peroxide which is suitably used include ketone peroxides such as PERHEXA H, peroxyketals such as PERHEXA TMH, hydroperoxides such as PERBUTYL H-69, dialkyl peroxides such as PERCUMYL D, PERBUTYL C and PERBUTYL D, diacyl peroxides such as NYPER BW, peroxyesters such as PERBUTYL Z and PERBUTYL L, and peroxydicarbonates such as PEROYL TCP, with those listed under trade names being commercially available from NOF CORPORATION; diisobutyryl peroxide, cumyl peroxyneodecanoate, di-n-propyl peroxydicarbonate, diisopropyl peroxydicarbonate, di-sec-butyl peroxydicarbonate, 1,1,3,3-tetramethylbutyl peroxyneodecanoate, di(4-t-butylchlorohexyl)peroxydicarbonate, di(2-ethylhexyl)peroxydicarbonate, t-hexyl peroxyneodecanoate, t-butyl peroxyneodecanoate, t-butyl peroxyneoheptanoate, t-hexyl peroxypivalate, t-butyl peroxypivalate, di(3,5,5-trimethylhexanoyl)peroxide, dilauroyl peroxide, 1,1,3,3-tetramethylbutyl peroxy-2-ethylhexanoate, disuccinic acid peroxide, 2,5-dimethyl-2,5-di(2-ethylhexanoylperoxy)hexane, t-hexyl peroxy-2-ethylhexanoate, di(4-methylbenzoyl)peroxide, t-butyl peroxy-2-ethylhexanoate, di(3-methylbenzoyl)peroxide, benzoyl(3-methylbenzoyl)peroxide, dibenzoyl peroxide, 1,1-di(t-butylperoxy)-2-methylcyclohexane, 1,1-di(t-hexylperoxy)-3,3,5-trimethylcyclohexane, 1,1-di(t-hexylperoxy)cyclohexane, 1,1-di(t-butylperoxy)cyclohexane, 2,2-di(4,4-di(t-butylperoxy) cyclohexyl)propane, t-hexylperoxyisopropyl monocarbonate, t-butyl peroxymaleic acid, t-butyl peroxy-3,5,5-trimethylhexanoate, t-butyl peroxylaurate, t-butyl peroxyisopropylmonocarbonate, t-butyl peroxy-2-ethylhexylmonocarbonate, t-hexyl peroxybenzoate, 2,5-dimethyl-2,5-di(benzoylperoxy)hexane, t-butyl peroxyacetate, 2,2-di(t-butylperoxy)butane, t-butyl peroxybenzoate, n-butyl-4,4-di-t-butyl peroxyvalerate, di(2-t-butylperoxyisopropyl)benzene, dicumyl peroxide, di-t-hexyl peroxide, 2,5-dimethyl-2,5-di(t-butylperoxy)hexane, t-butylcumyl peroxide, di-t-butyl peroxide, p-methane hydroperoxide, 2,5-dimethyl-2,5-di(t-butylperoxy)hexyne-3, diisopropylbenzene hydroperoxide, 1,1,3,3-tetramethylbutyl hydroperoxide, cumene hydroperoxide, t-butyl hydroperoxide, 2,3-dimethyl-2,3-diphenylbutane, 2,4-dichlorobenzoyl peroxide, o-chlorobenzoyl peroxide, p-chlorobenzoyl peroxide, tris-(t-butylperoxy)triazine, 2,4,4-trimethylpentyl peroxyneodecanoate, α-cumyl peroxyneodecanoate, t-amyl peroxy-2-ethylhexanoate, t-butyl peroxyisobutyrate, di-t-butyl peroxyhexahydroterephthalate, di-t-butyl peroxytrimethyladipate, di-3-methoxybutyl peroxydicarbonate, di-isopropyl peroxydicarbonate, t-butyl peroxyisopropylcarbonate, 1,6-bis(t-butylperoxycarbonyloxy)hexane, diethylene glycol bis(t-butylperoxycarbonate), t-hexyl peroxyneodecanoate; as well as Luperox 11 commercially available from ARKEMA Yoshitomi, Ltd.

Examples of the organic azo compound which is suitably used include azonitrile compounds such as V-30, V-40, V-59, V-60, V-65 and V-70, azoamide compounds such as VA-080, VA-085, VA-086, VF-096, VAm-110 and VAm-111, cyclic azoamidine compounds such as VA-044 and VA-061, azoamidine compounds such as V-50 and VA-057, and azoester compounds such as V-601, with those listed under trade names being commercially available from Wako Pure Chemical Industries, Ltd.; 2,2-azobis(4-methoxy-2,4-dimethylvaleronitrile), 2,2-azobis(2,4-dimethylvaleronitrile), 2,2-azobis(2-methylpropionitrile), 2,2-azobis(2,4-dimethylbutyronitrile), 1,1-azobis(cyclohexane-1-carbonitrile), 1-[(1-cyano-1-methylethyl)azo]formamide, 2,2-azobis{2-methyl-N-[1,1-bis(hydroxymethyl)-2-hydroxyethyl]propionamide}, 2,2-azobis[2-methyl-N-(2-hydroxybutyl)propionamide], 2,2-azobis[N-(2-propenyl)-2-methylpropionamide], 2,2-azobis(N-butyl-2-methylpropionamide), 2,2-azobis(N-cyclohexyl-2-methylpropionamide), 2,2-azobis[2-(2-imidazolin-2-yl)propane]dihydrochloride, 2,2-azobis[2-(2-imidazolin-2-yl)propane]disulfate dihydrate, 2,2-azobis{2-[1-(2-hydroxyethyl)-2-imidazolin-2-yl]propane}dihydrochloride, 2,2-azobis[2-[2-imidazolin-2-yl]propane], 2,2-azobis(1-imino-1-pyrrolidino-2-methylpropane)dihydrochloride, 2,2-azobis(2-methylpropionamidine)dihydrochloride, 2,2-azobis[N-(2-carboxyethyl)-2-methylpropionamidine]

tetrahydrate, dimethyl 2,2-azobis(2-methylpropionate), 4,4-azobis(4-cyanovaleric acid), as well as 2,2-azobis(2,4,4-trimethylpentane).

Organic azo compounds are preferable as a polymerization initiator in view of the safety of a reagent in itself and the molecular weight-reproducing property of a polymerization reaction. Particularly preferred are azoester compounds such as V-601 because the polymer which is prepared using an azoester compound is free of noxious cyano.

Preferably, the ten hour half-life temperature of a polymerization initiator does not exceed 100° C. A polymerization initiator with a ten hour half-life temperature of 100° C. or lower is easy to make lost at the end of reaction.

For the polymerization as above, only one initiator or two or more initiators mixed together may be used.

The amount of a polymerization initiator used is preferably 0.0001 to 2 moles, more preferably 0.003 to 1 moles, and even more preferably 0.001 to 0.5 moles per mole of monomer.

The weight-average molecular weight ($M_w$) of the polymer at the end of polymerization reaction is preferably $2 \times 10^4$ to $50 \times 10^4$, more preferably $3 \times 10^4$ to $40 \times 10^4$, and most preferably $4 \times 10^4$ to $40 \times 10^4$.

The Z+1-average molecular weight ($N_{Z+1}$) of the polymer at the end of polymerization reaction is preferably $10 \times 10^4$ to $60 \times 10^4$, more preferably $9 \times 10^4$ to $55 \times 10^4$, and most preferably $8 \times 10^4$ to $40 \times 10^4$.

It is preferable that the polymer at the end of polymerization reaction contains essentially no components with a molecular weight of $300 \times 10^4$ or higher, with an essential absence of components with a molecular weight of $200 \times 10^4$ or higher being more preferable, and it is most preferable that the polymer contains no components with a molecular weight of $100 \times 10^4$ or higher.

If polymerization is achieved under molecular weight conditions falling within the above ranges, a composition for film formation allowing the coating film whose surface state is improved and whose thickness less decreases during baking can be prepared with high yields.

During the production of compound (A), the reaction solution in which compound (I) has been polymerized may be used as such, while it is preferable to subject the solution to purification treatment after the reaction is terminated. Purification may be carried out in a conventional manner by a solution purification technique, such as liquid-liquid extraction to remove residual monomers and oligomer components by combining the rinse with water and the use of an appropriate solvent, ultrafiltration to extract and remove only those molecules whose molecular weight does not exceed a specified one, centrifugation, and column chromatography, or by a solid purification technique, such as reprecipitation to remove residual monomers and so forth by adding a polymer solution dropwise to a poor solvent to solidify the polymer of interest in the poor solvent, and purification by washing the polymer slurry separated by filtration with a poor solvent.

In an exemplary treatment, the solvent in which the polymer as described above is less soluble or insoluble (poor solvent) is brought into contact with the reaction solution in an amount by volume not more than ten times, preferably five to ten times, as large as that of the reaction solution to precipitate the polymer as solid. The solvent to be used during the precipitation or reprecipitation from the reaction solution (solvent for precipitation or reprecipitation) is not particularly limited as long as it is a poor solvent for the polymer, so that it is selected from among hydrocarbon, halogenated hydrocarbon, nitro compound, ether, ketone, ester, carbonate, alcohol, carboxylic acid, water, a mixture thereof, and so forth as appropriate to the type of the polymer. Among the above, a solvent containing at least alcohol (methanol in particular) or water is preferable as a solvent for precipitation or reprecipitation.

The amount of a solvent for precipitation or reprecipitation used may appropriately be selected taking the efficiency, the yield, and so forth into consideration, and is generally 100 to 10,000 parts by weight, preferably 200 to 2000 parts by weight, and more preferably 300 to 1000 parts by weight per 100 parts by weight of the polymer solution.

The temperature for precipitation or reprecipitation may appropriately be selected taking the efficiency and the convenience into consideration, and is generally about 0 to 50° C., while preferably in the vicinity of room temperature (e.g., about 20 to 35° C.). Precipitation or reprecipitation may be achieved by a known batch method or continuous method using a conventional mixing vessel such as an agitating tank.

The polymer as precipitated or reprecipitated is generally subjected to a conventional solid-liquid separation such as filtration and centrifugation, and dried to use. Filtration is performed using a solvent-resistant filter, and preferably under pressure. Drying is performed under a normal or reduced pressure (reduced pressure being preferred) at a temperature of about 30 to 100° C., preferably about 30 to 50° C.

It is also possible that the polymer as precipitated and separated is dissolved again in a good solvent, and the resultant solution is brought into contact with the solvent in which the polymer is less soluble or insoluble. In other words, the purification method may include bringing the solvent in which the polymer is less soluble or insoluble into contact with the reaction solution after the termination of polymerization reaction to precipitate the polymer (step a), separating the polymer from the solution (step b), newly dissolving the polymer in a good solvent to prepare polymer solution A (step c), then bringing the solvent in which the polymer is less soluble or insoluble into contact with polymer solution A in an amount by volume less than ten times (preferably not more than five times) as large as that of polymer solution A to precipitate the polymer in solid form (step d), and separating the precipitated polymer (step e).

Preferred good solvents include ethyl acetate, butyl acetate, toluene, methyl ethyl ketone, and tetrahydrofuran. The good solvent is preferably used in an amount by weight equal to or up to 50 times as large as that of the polymer of the present invention, more preferably in a 2 to 20 times larger amount by weight.

A polymerization inhibitor may be added in order to prevent excess polymerization in a polymer of compound (I) or in the process for producing the polymer. Exemplary polymerization inhibitors include 4-methoxyphenol, 2,6-bis(1,1-dimethylethyl)-4-methyl phenol, and catechol.

<Compound (B) Having a Conjugated Diene Structure>

Compound (B) having a conjugated diene structure is the compound having a conjugated diene structure that can show Diels-Alder reaction with compound (A) as described above. The conjugated diene structure of compound (B) is not particularly limited, with examples including the exemplary structures as mentioned before. It should be noted that compound (B) having a conjugated diene structure may be used singly or as a combination of two or more different compounds (B).

Any compound with a conjugated diene skeleton is available as a compound having a conjugated diene structure, whereupon volatile, low molecular-weight dienes are preferable. Examples of the compound having a conjugated diene structure include those compounds described as dienes in: "Dienes in the Diels-Alder Reaction" (Wiley InterScience, 1990); "The Diels-Alder Reaction: Selected Practical Methods" (John Wiley & Sons, Inc., 2002).

Examples of the compound having a conjugated diene structure also include hydrocarbon compounds having a conjugated diene structure, to be more specific, 1,3-butadiene, isoprene, 1,3-pentadiene, 1,3-hexadiene, 1,3-octadiene, ethylidene norbornene, vinyl norbornene, dicyclopentadiene, cyclopentadiene, pentamethyl cyclopentadiene, 4-ethylidene-8-methyl-1,7-nonadiene, 2,3-dimethyl-1,3-butadiene, 2-methyl-1,3-pentadiene, 4,5-diethyl-1,3-octadiene, 3-butyl-1,3-octadiene, 1,3,7-octatriene, cyclooctadiene, norbornadiene, 1,3,5,5-tetramethyl-1,3-cyclohexadiene, α-phellandrene, α-terpinene, 1,2,3,4-tetraphenyl-1,3-cyclopentadiene, 1,2,3,4,5-pentaphenyl-1,3-cyclopentadiene, tetraphenyl cyclopentadienone, furan, thiophene, pyrrole, N-methylpyrrole, and N-phenyl pyrrole.

Among the above, dicyclopentadiene, cyclopentadiene, pentamethyl cyclopentadiene, α-phellandrene, α-terpinene, and tetraphenyl cyclopentadienone are preferable.

Preferred examples of the above compound having a conjugated diene structure include compounds represented by general formulae (B-1) through (B-3). If any such compound is used, Diels-Alder reaction proceeds with high yields and, accordingly, a film obtained has a further reduced dielectric constant and a higher Young's modulus of elasticity, and is stable for a long period of time.

[Chemical Formula 17]

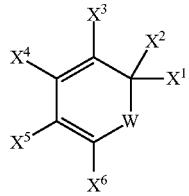

General formula (B-1)

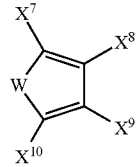

General formula (B-2)

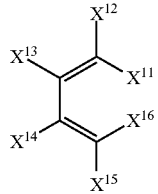

General formula (B-3)

In general formulae (B-1) through (B-3), $X^1$ to $X^{16}$ are each independently a hydrogen atom or a substituent.

In general formulae (B-1) and (B-2), W is —O—, —C(O)—, —C(O)O—, —S(O)—, —S(O)$_2$—, —C($X^{17}$)($X^{18}$)—, or —N($X^{19}$)—, with $X^{17}$ to $X^{19}$ being each independently a hydrogen atom or a substituent.

In general formula (B-1), $X^1$ to $X^{16}$ are each independently a hydrogen atom or a substituent. The substituents as represented by $X^1$ to $X^{16}$ are defined identically to those represented by $Y^1$ to $Y^{11}$ in general formulae (F-1) through (F-4). Among others, an alkyl group, a cycloalkyl group, an aryl group, a silicon atom-containing group, and so forth are preferable.

$X^{17}$ to $X^{19}$ are each independently a hydrogen atom or a substituent. The substituents as represented by $X^{17}$ to $X^{19}$ are defined identically to those represented by $X^1$ to $X^{16}$ as above.

If a coating film containing compound (Y) obtained by binding compound (B) having a diene structure as described above to compound (A) having a siloxane structure is subjected to curing treatment by heating, irradiation with light, irradiation with radiation, or a combination thereof, retro Diels-Alder reaction occurs. Upon the reaction, compound (B) having a diene structure that acts as a pore forming agent volatilizes from compound (Y) to increase the film porosity and, in addition, a curing reaction occurs between remaining groups. As a consequence, a film exhibiting a low dielectric constant, a high refractive index, a high mechanical strength, a high resistance to heat and a high resistance to oxidation stress, with its dielectric constant being stable over a long period of time, can be fabricated.

The addition amount (content) of the compound having a diene structure in compound (Y) is preferably 5 to 80% by weight, more preferably 5 to 60% by weight, and even more preferably 10 to 50% by weight based on the total amount of compound (Y). An addition amount falling within the above range prevents formation of communicating pores, and is desirable for a flat film. The addition amount of the compound having a diene structure may be determined from an NMR spectrum, or by thermogravimetric analysis (TGA) measuring weight variations under heating or cooling conditions, or differential thermal analysis (DTA) or differential scanning calorimetry (DSC) measuring the variation in specific heat or heat of reaction.

If compound (Y) as synthesized by using compound (B) is used in the present invention, the dienophile structure which is capable of serving as a crosslinking moiety is generated during the curing of a film, concurrently with the release of compound (B) acting as a pore forming agent. In consequence, pore formation and crosslinkage proceed at a time in the same area in the film, so that many pores of a smaller, uniform size are formed evenly in the film. In contrast, a film merely provided with large-sized pores with a nonuniform size distribution and having an inadequate mechanical strength is fabricated using a known pore forming agent because known pore forming agents are generally so cohesive as to form large domains and, accordingly, cause the area where a pore forming agent volatilizes and the area where a crosslinked structure is formed to be separated from each other.

In the present invention, use of compound (Y) brings about the siloxane-structured film which is relatively high in gas permeability, and such a film is expected to make compound (B) volatilize more readily, leading to the formation of pores with a desired size.

<Reaction Conditions>

Conditions for Diels-Alder reaction between compound (A) and compound (B) as described above are selected as most appropriate to the type of compounds used, and so forth.

The solvent to be used for Diels-Alder reaction is not particularly limited as long as compounds used are soluble in the solvent, and the reaction is not affected by the solvent. Examples include the solvents which may be used for the polymerization reaction of compound (I) as described before.

The reaction temperature is not particularly limited, and is generally 25 to 250° C., while preferably 50 to 200° C., and more preferably 80 to 200° C.

The concentration of compound (A) in the reaction solution is preferably 30% by weight or lower, more preferably 20% by weight or lower, and even more preferably 15% by weight or lower based on the total amount of the reaction solution. Compound (A) concentrations falling within the above range can prevent generation of impurities such as gelatinized components.

The reaction is preferably conducted in an inert atmosphere (e.g., nitrogen gas, argon gas) in order to prevent inactivation of the polymerization initiator by oxygen. The oxygen concentration during the reaction is preferably 100 ppm or less, more preferably 50 ppm or less, and even more preferably 20 ppm or less.

After the termination of reaction, the solution is preferably subjected to the purification treatment as described before with respect to the production of compound (A).

In the process for producing compound (Y), it is preferable to add a polymerization inhibitor in order to prevent polymerization reaction. Exemplary polymerization inhibitors include 4-methoxyphenol, 2,6-bis(1,1-dimethylethyl)-4-methyl phenol, and catechol. Among others, 4-methoxyphenol and 2,6-bis(1,1-dimethylethyl)-4-methyl phenol are preferable. The amount of a polymerization inhibitor added is preferably not less than 5% by weight on the total amount of compound (A) having a siloxane structure.

<Composition>

The composition of the present invention contains compound (X) as described above. The composition of the present invention may be a solution containing compound (X) dissolved in a solvent (e.g., organic solvent), or a solid containing reactants of compound (X) synthesis.

The composition of the present invention is widely applicable, and the compound (X) content, the additives to be used, and so forth are selected in accordance with the intended use. The inventive composition may be used for the fabrication of a film (insulator film, for instance) (as a composition for film formation), or as a low refractive index film, a low refractive index material, a gas adsorption material or a resist material.

Among the solid components contained in the composition, compound (X) is not particularly limited in content. The compound, however, preferably comprises not less than 70% by weight, more preferably not less than 80% by weight, and most preferably not less than 90% by weight of the total solid components if the composition is to be used for the film fabrication as described later. As compound (X) comprises a higher percent of the solid components, the composition is more improved in applicability, and a film with a further reduced dielectric constant can be formed. In this regard, the term "solid components" means the components as future constituents of the film as described later, that is to say, components exclusive of the solvent and the like.

If compound (X) is to be produced by using compounds (A) and (B) as described above, the total of unreacted compound (A) and unreacted compound (B) having a conjugated diene structure preferably comprises not more than 15% by weight, more preferably not more than 10% by weight, and even more preferably not more than 7% by weight of the total solid components contained in the composition of the present invention. Amounts of compounds (A) and (B) in total falling within the above range allow the coating film of low dielectric constant whose surface state is further improved.

The composition of the present invention may contain a solvent. In other words, compound (X) is preferably dissolved in an appropriate solvent so as to apply it onto a support.

Preferred are those solvents which dissolve not less than 5% by weight of compound (X) at 25° C., with those dissolving not less than 10% by weight being more preferred. To be more specific, preferred solvents are exemplified by ethylene dichloride, cyclohexanone, cyclopentanone, 2-heptanone, methyl isobutyl ketone, γ-butyrolactone, methyl ethyl ketone, methanol, ethanol, dimethyl imidazolidinone, ethylene glycol monomethyl ether, ethylene glycol monoethyl ether, ethylene glycol dimethyl ether, 2-methoxyethyl acetate, ethylene glycol monoethyl ether acetate, propylene glycol monomethyl ether (PGME), propylene glycol monomethyl ether acetate (PGMEA), tetraethylene glycol dimethyl ether, triethylene glycol monobutyl ether, triethylene glycol monomethyl ether, isopropanol, ethylene carbonate, ethyl acetate, butyl acetate, methyl lactate, ethyl lactate, methyl methoxypropionate, ethyl ethoxypropionate, methyl pyruvate, ethyl pyruvate, propyl pyruvate, N,N-dimethylformamide, dimethylacetamide, dimethyl sulfoxide, N-methylpyrrolidone, tetrahydrofuran, diisopropyl benzene, toluene, xylene, and mesitylene. These solvents are used separately or as a mixture.

Among the above, desirable are propylene glycol monomethyl ether acetate, propylene glycol monomethyl ether, 2-heptanone, cyclohexanone, γ-butyrolactone, ethylene glycol monomethyl ether, ethylene glycol monoethyl ether, ethylene glycol monoethyl ether acetate, propylene glycol monomethyl ether, propylene glycol monoethyl ether, ethylene carbonate, butyl acetate, methyl lactate, ethyl lactate, methyl methoxypropionate, ethyl ethoxypropionate, N-methylpyrrolidone, N,N-dimethylformamide, tetrahydrofuran, methyl isobutyl ketone, xylene, mesitylene, and diisopropyl benzene.

A solution obtained by dissolving the composition of the present invention in an appropriate solvent is also encompassed by the composition of the present invention. If the composition is to be made to contain a solvent, the concentration of the total solid components in the composition is preferably 1 to 30% by weight based on the total amount of the composition, and is controlled as appropriate to the intended use of the composition. If the total solid concentration of the composition is 1 to 30% by weight, the thickness of a coating film will fall within an adequate range, and the storage stability of a coating solution will be more excellent.

The composition of the present invention may contain a polymerization initiator. It is preferable that a polymerization initiator is contained in the composition of the present invention especially if a film formed of the composition should be cured at lower temperatures. In that case, the polymerization initiator to be contained is not particularly limited in type but exemplified by initiators for use in the polymerization of compound (I) as described before. It is also possible to use an initiator inducing radiation polymerization, so as to promote curing at lower temperatures.

It is preferred that the content of metal as an impurity in the composition of the present invention is well reduced. The metal concentration of the composition can be measured with high sensitivity by an ICP-MS method or the like, whereupon, with respect to the metals other than transition metals, the metal content is preferably 30 ppm or lower, more preferably 3 ppm or lower, and even more preferably 300 ppb or lower. Transition metals, as being high in catalytic ability to accelerate oxidation, increase the dielectric constant of a film obtained according to the present invention by way of oxidation reaction in the prebaking or heat-curing process as described later, so that a lower transition metal content is more preferable. In fact, the transition metal content is preferably 10 ppm or lower, more preferably 1 ppm or lower, and even more preferably 100 ppb or lower.

The metal concentration of the composition may also be evaluated by conducting a total reflection fluorescent X-ray analysis on a film obtained by using the composition. If a tungsten wire is employed as an X-ray source, K, Ca, Ti, Cr, Mn, Fe, Co, Ni, Cu, Zn, and Pd can be observed as metal elements, whereupon each metal is preferably $100 \times 10^{10}$ cm$^2$ or less, more preferably $50 \times 10^{10}$ cm$^{-2}$ or less, and even more preferably $10 \times 10^{10}$ cm$^{-2}$ or less in residual amount. Bromine as a halogen is also observable, with the residual amount thereof being preferably $10,000 \times 10^{10}$ cm$^{-2}$ or less, more preferably $1000 \times 10^{10}$ cm$^{-2}$ or less, and even more preferably $400 \times 10^{10}$ cm$^{-2}$ or less. Another observable halogen is chlorine, whose residual amount is preferably $100 \times 10^{10}$ cm$^{-2}$ or less, more preferably $50 \times 10^{10}$ cm$^{-2}$ or less, and even more preferably $10 \times 10^{10}$ cm$^{-2}$ or less in view of the fact that it may cause damage on a CVD apparatus, an etching apparatus, and so forth.

<Additives>

To the composition of the present invention, such an additive as a radical generator, colloidal silica, a surfactant and an adhesive agent may be added as long as the properties (heat resistance, dielectric constant, mechanical strength, applicability, adhesion, and so forth) of a film obtained by using the composition are not impaired.

Any colloidal silica is usable for the composition of the present invention as long as it does not prevent the achievement of the object of the present invention. As an example, the dispersion prepared by dispersing silicic anhydride of high purity in a hydrophilic organic solvent or water, whose mean particle size is generally 5 to 30 nm, and preferably 10 to 20 nm, and whose solid concentration is about 5 to 40% by weight, is mentioned.

Any surfactant is usable for the composition of the present invention as long as it does not prevent the achievement of the object of the present invention. Examples include nonionic surfactants, anionic surfactants and cationic surfactants, more specifically, silicone-based surfactants, fluorine-containing surfactants, polyalkylene oxide-based surfactants, and acrylic surfactants. The surfactant to be used may be a single surfactant, or a combination of two or more surfactants. Silicone-based surfactants, nonionic surfactants, fluorine-containing surfactants, and acrylic surfactants are preferable, with silicone-based ones being particularly preferred.

The surfactant used in the present invention is preferably added in an amount of 0.01 to 1% by weight, more preferably of 0.01 to 0.5% by weight, of the total amount of the composition.

In the present invention, a silicone-based surfactant refers to a surfactant containing at least one Si atom. Any silicone-based surfactant is usable in the present invention, whereupon the surfactant to be used is preferably of a structure containing alkylene oxide and dimethyl siloxane. More preferably, the surfactant is of a structure containing a moiety represented by the chemical formula as below.

[Chemical Formula 18]

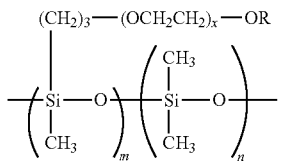

In the formula, R is a hydrogen atom or an alkyl group with 1 to 5 carbon atoms, x is an integer of 1 to 20, as well as m and n are each independently an integer of 2 to 100. Rs in the structure may or may not be the same.

Examples of the silicone-based surfactant which may be used in the present invention include BYK-306 and BYK-307 (BYK Japan KK), SH7PA, SH21PA, SH28PA and SH30PA (Dow Corning Toray Silicone Co., Ltd.), as well as Troysol S366 (Troy Chemical Industries, Inc.).

Any nonionic surfactant is usable in the present invention as long as it does not prevent the achievement of the object of the present invention. Exemplary nonionic surfactants include polyoxyethylene alkyl ethers, polyoxyethylene aryl ethers, polyoxyethylene dialkyl esters, sorbitan fatty acid esters, fatty acid-modified polyoxyethylenes, and polyoxyethylene-polyoxypropylene block copolymers.

Any fluorine-containing surfactant is usable in the present invention as long as it does not prevent the achievement of the object of the present invention. Exemplary surfactants include perfluorooctyl polyethylene oxide, perfluorodecyl polyethylene oxide, and perfluorododecyl polyethylene oxide.

Any acrylic surfactant is usable in the present invention as long as it does not prevent the achievement of the object of the present invention. As an example, a (meth)acrylic copolymer is mentioned.

Any adhesion promoter is usable for the composition of the present invention as long as it does not prevent the achievement of the object of the present invention. Exemplary adhesion promoters include 3-glycidyloxypropyl trimethoxysilane, 3-aminoglycidyloxypropyl triethoxysilane, 3-glycidyloxypropylmethyl dimethoxysilane, 3-aminopropyl trimethoxysilane, 1-methacryloxypropylmethyl dimethoxysilane, 3-aminopropyl triethoxysilane, 2-aminopropyl trimethoxysilane, 2-aminopropyl triethoxysilane, N-(2-aminoethyl)-3-aminopropyl trimethoxysilane, N-(2-aminoethyl)-3-aminopropylmethyl dimethoxysilane, 3-ureidopropyl trimethoxysilane, 3-ureidopropyl triethoxysilane, N-ethoxycarbonyl-3-aminopropyl trimethoxysilane, N-ethoxycarbonyl-3-aminopropyl triethoxysilane, N-triethoxysilylpropyl triethylene triamine, N-trimethoxysilylpropyl triethylene triamine, 10-trimethoxysilyl-1,4,7-triazadecane, 10-triethoxysilyl-1,4,7-triazadecane, 9-trimethoxysilyl-3,6-diazanonyl acetate, 9-triethoxysilyl-3,6-diazanonyl acetate, N-benzyl-3-aminopropyl triethoxysilane, N-phenyl-3-aminopropyl trimethoxysilane, N-phenyl-3-aminopropyl triethoxysilane, N-bis(oxyethylene)-3-aminopropyl trimethoxysilane, N-bis(oxyethylene)-3-aminopropyl triethoxysilane, trimethoxysilyl benzoate, 3-methacryloxypropyl trimethoxysilane, vinyl triacetoxysilane, vinyl trimethoxysilane, γ-isocyanatopropyl triethoxysilane, γ-glycidoxypropyl trimethoxysilane, β-(3,4-epoxycyclohexyl)ethyl trimethoxysilane, trimethoxyvinyl silane, γ-aminopropyl triethoxysilane, N-benzyl-3-aminopropyl trimethoxysilane, aluminum monoethylacetoacetate diisopropylate, vinyl tris(2-methoxyethoxy)silane, N-(2-aminoethyl)-3-aminopropylmethyl dimethoxysilane, N-(2-aminoethyl)-3-aminopropyl trimethoxysilane, 3-chloropropylmethyl dimethoxysilane, 3-chloropropyl trimethoxysilane, 3-methacryloxypropyl trimethoxysilane, 3-mercaptopropyl trimethoxysilane, trimethyl chlorosilane, dimethyl vinyl chlorosilane, methyl diphenyl chlorosilane, chloromethyl dimethyl chlorosilane, trimethyl methoxysilane, dimethyl diethoxysilane, dimethyl vinyl ethoxysilane, diphenyl dimethoxysilane, phenyl triethoxysilane, hexamethyl disilazane, N,N'-bis(trimethylsilyl)urea, dimethyl trimethylsilyl amine, trimethylsilyl imidazole, vinyl trichlorosilane, benzotriazole, benzimidazole, indazole, imidazole, 2-mercaptobenzimidazole, 2-mercaptobenzothiazole, 2-mercaptobenzoxazole, urazole, thiouracil, mercaptoimidazole, mercaptopyrimidine, 1,1-dimethyl urea, 1,3-dimethyl urea, and a thiourea compound. Functional silane coupling agents are preferable as an adhesion promoter. In the present invention, a single adhesion promoter or a combination of two or more adhesion promoters may be used.

The amount of an adhesion promoter used is not particularly limited, while it is generally not more than 10% by weight on the amount of the total solid components in the composition, with amounts of 0.05 to 5% by weight being particularly preferred.

The composition of the present invention is preferably filtrated through a filter to remove insolubles, gelatinated components, and so forth before it is used for film formation. The pore size of the filter is preferably 0.005 to 0.5 µm, more preferably 0.005 to 0.2 µm, and most preferably 0.005 to 0.1 µm. Preferred filter materials are polytetrafluoroethylene, polyethylene, polypropylene and nylon, with polytetrafluoroethylene, polyethylene and nylon being more preferred.

<Film Fabrication>

As mentioned before, the composition of the present invention is widely applicable. For instance, the inventive composition may be used for the fabrication of an insulator film. (Hereafter, the inventive composition is optionally referred to as "composition for film formation").

The insulator film which is to be obtained by using the composition for film formation of the present invention may be fabricated by applying the composition for film formation onto a substrate such as silicon wafer, $SiO_2$ wafer, SiN wafer, glass, or plastic film by a specified technique, including spin coating, roller coating, dip coating, scan coating, spray coating and bar coating, then removing a solvent as required by heating treatment.

The method for application to a substrate is preferably based on spin coating or scan coating, especially on spin coating. Spin coating may be carried out using a commercially available system. Systems of CLEAN TRACK Series (manufactured by Tokyo Electron Limited), D-SPIN Series (manufactured by DAINIPPON SCREEN MFG. CO., LTD.), and of SS or CS Series (manufactured by TOKYO OHKA KOGYO CO., LTD.), for instance, are suitable for use.

Any rotation speed will do as a spin coating condition, while a rotation speed of about 1300 rpm is preferable for a 300 mm silicon substrate from the viewpoint of the in-plane uniformity of an insulator film formed. A solution of the composition may be ejected dynamically onto a rotating substrate, or statically onto a substrate at rest, with dynamic ejection being preferable from the viewpoint of the in-plane uniformity of a film. It is also possible that only a principal solvent for the composition is previously ejected onto a substrate to form a liquid film thereon, then the composition is ejected onto the liquid film so as to save the composition. The spin coating time is not particularly limited, while it is within 180 seconds for a favorable throughput. Taking the transport of substrates into account, it is preferable to conduct certain treatment (edge rinsing, back rinsing) so as to prevent the film as formed from remaining on edges of the substrate.

Heat treatment is not particularly limited in method therefor, and may be conducted by a conventional method, such as hot plate heating, heating with a furnace, and heating by irradiation with light from a xenon lamp using a rapid thermal processor (RTP) or the like. Hot plate heating and heating with a furnace are preferable. In this regard, a commercially available system of CLEAN TRACK Series (manufactured by Tokyo Electron Limited), D-SPIN Series (manufactured by DAINIPPON SCREEN MFG. CO., LTD.), SS or CS Series (manufactured by TOKYO OHKA KOGYO CO., LTD.) or the like may suitably be used as a hot plate. A system of a Series (manufactured by Tokyo Electron Limited), for instance, may be suitable as a furnace.

The composition of the present invention as applied onto a substrate to form it into a coating film is preferably subjected to curing treatment. During the curing treatment, the composition (coating film) on the substrate is cured so as to make the coating film resistant to solvent. Heating treatment (baking) is particularly preferable as a method of curing the film. The polymerization reaction between vinyl groups remaining in compound (X) that occurs during post-heating may be utilized, for instance. With respect to the conditions for post-heating treatment, the temperature is preferably 100 to 600° C., more preferably 200 to 500° C., and even more preferably 200 to 400° C., and the treatment time is preferably one minute to three hours, more preferably one minute to two hours, and even more preferably one minute to one hour. The post-heating treatment may be conducted in several steps. It is particularly preferable for the prevention of thermal oxidation with oxygen to carry out post-heating in a nitrogen atmosphere.

In the present invention, a film of the composition may be cured through the polymerization reaction between vinyl or ethynyl groups remaining in compound (X) that is caused not by heating treatment but irradiation with a high energy beam such as light or radiation. Exemplary high energy beams include electron beam, ultraviolet light and X-ray, although the irradiation method is in no way limited to such.

If an electron beam is to be used as the high energy beam, the beam energy is preferably 0.1 to 50 keV, more preferably 0.2 to 30 keV, and even more preferably 0.5 to 20 keV. The total electron beam dose is preferably 0.01 to 5 $\mu C/cm^2$, more preferably 0.01 to 2 $\mu C/cm^2$, and even more preferably 0.01 to 1 $\mu C/cm^2$. During irradiation with an electron beam, the substrate temperature is preferably 0 to 500° C., more preferably 20 to 450° C., and even more preferably 20 to 400° C. The pressure is preferably 0 to 133 kPa, more preferably 0 to 60 kPa, and even more preferably 0 to 20 kPa.

From the viewpoint of preventing oxidation of the polymer of the present invention, it is preferable to use an inert atmosphere such as Ar, He and nitrogen gases as an atmosphere surrounding a substrate. Oxygen gas, hydrocarbon gas, or ammonia gas may be added in order to react it with plasma, electromagnetic wave or chemical species generated by the interaction with an electron beam. Irradiation with an electron beam may be performed several times and, in that case, the conditions for irradiation with an electron beam do not need to be every time the same but, on the contrary, may every time be different.

The high energy beam may also be ultraviolet light. The wavelength region of the ultraviolet light to be used for irradiation is preferably 160 to 400 nm, and the output thereof is preferably 0.1 to 2000 $mWcm^{-2}$ just on a substrate. During irradiation with ultraviolet light, the substrate temperature is preferably 250 to 450° C., more preferably 250 to 400° C., and even more preferably 250 to 350° C. From the viewpoint of preventing oxidation of the polymer of the present invention, it is preferable to use an inert atmosphere such as Ar, He and nitrogen gases as an atmosphere surrounding a substrate. The pressure is preferably 0 to 133 kPa.

A film of the inventive composition may be cured by conducting heating treatment and irradiation treatment with a high energy beam such as light or radiation simultaneously or sequentially.

If an insulator film is to be fabricated, a coating film with a dry thickness of about 0.05 to 1.5 µm can be formed by one-time application of the composition, and a coating film with a dry thickness of about 0.1 to 3 µm by two-time application.

In order that cage structure may not be decomposed during baking, it is preferable that a group making nucleophilic attack on a Si atom during the preparation of a composition and the fabrication of a film (e.g., hydroxy group, silanol group) is essentially absent.

To be more specific: An insulator film of low dielectric constant can be fabricated by applying the composition for film formation of the present invention onto a substrate (substrate with metal wiring in general) by, for instance, a spin coating technique, drying the solvent by a preliminary heating treatment, then conducting the final heating treatment (annealing) at a temperature of 300 to 430° C.

<Insulator Film>

The insulator film obtained from the composition for film formation as described above is not particularly limited in thickness, while its thickness is preferably 0.005 to 10 μm, more preferably 0.01 to 5.0 μm, and even more preferably 0.01 to 1.0 μm.

In this regard, it is assumed that the thickness of the insulator film of the present invention is found as the arithmetic mean of values obtained by measuring the thickness at any three or more points by an optical interferometric film thickness-measuring instrument.

The relative dielectric constant of the insulator film obtained according to the method of the present invention as described above varies with materials used, while preferably not more than 2.4, that is to say, 1.8 to 2.4 as measured at a temperature of 25° C.

The Young's modulus of elasticity of the inventive insulator film varies with materials used, while preferably 2.0 to 15.0 GPa, and more preferably 3.0 to 15.0 GPa.

The film obtained from the composition for film formation as described above is preferably a porous film having the pore distribution curve on which the maximum peak appears preferably at a pore diameter of not more than 5 nm (such a pore diameter being hereafter also referred to as "maximum distributed diameter"). If the maximum distributed diameter is not more than 5 nm, a better mechanical strength and a higher relative dielectric constant are compatible with each other.

More preferably, the maximum distributed diameter is not more than 3 nm. While the maximum distributed diameter is not particularly limited in its lowest value, the lowest value which is measurable with a known measuring instrument may be 0.5 nm.

The maximum distributed diameter refers to the pore diameter at which the maximum peak appears on a pore distribution curve obtained by a nitrogen gas adsorption technique.

If the insulator film obtained by using the composition for film formation of the present invention is to be used as an interlayer insulator film for a semiconductor device, the film may be provided on its side facing the wiring structure of the device with a barrier layer for preventing metal migration. On the upper or lower side of the wiring or the interlayer insulator film, not only a cap layer or interlayer adhesive layer for preventing detachment during chemical mechanical polishing (CMP) but an etching stopper layer and so forth may be provided. Moreover, the interlayer insulator film may be composed of a plurality of layers of different materials as required.

The insulator film of the present invention may be used in the form of a laminate with other Si-containing insulator film or an organic film. A laminate with a hydrocarbon-based film is preferred.

The insulator film obtained by using the composition for film formation of the present invention may be etched for copper wiring or another purpose. Either of wet etching and dry etching will do, while dry etching is preferable. In dry etching, both ammonia plasma and fluorocarbon plasma are usable as appropriate. For such plasmae, oxygen gas, nitrogen gas, hydrogen gas or helium gas may be used apart from Ar gas. The etching process may be followed by an ashing process for removing the photoresist or the like as used for etching, and further by a washing process for removing residues left upon ashing.

The insulator film obtained by using the composition for film formation of the present invention may be subjected to CMP after the copper wiring process in order to planarize copper-plated portions. The CMP slurry (chemical solution) to be used may be a commercially available slurry (product of Fujimi Incorporated, RODEL NITTA COMPANY, JSR Corporation, Hitachi Chemical Company, Ltd. or the like) selected as appropriate. Similarly, a commercially available CMP system (manufactured by Applied Materials, Inc., EBARA CORPORATION or the like) is appropriately usable. The CMP may be followed by a washing process for removing slurry residues.

<Uses>

The insulator film of the present invention is widely applicable, and particularly suitable for electronic devices. The term "electronic device" as used herein means any of a wide variety of electronic equipment including a semiconductor device and a magnetic recording head. The inventive film is suitable as, for instance, an insulator film in a semiconductor device such as an LSI, a system LSI, a DRAM, an SDRAM, an RDRAM and a D-RDRAM, or in an electronic component such as a laminate multichip module. In addition, the inventive film is applicable as a passivation film or an α-ray blocking film in an LSI, a coverlay film or an overcoat film of a flexographic printing plate, a cover coat or a solder resist film of a flexible copper-clad laminate, and a liquid crystal orienting film, as well as an interlayer insulator film for a semiconductor device, an etching stopper film, a surface-protective film and a buffer coat. The inventive film is also applicable as a surface-protective film, an antireflection coating and a phase difference film for an optical instrument.

EXAMPLES

The present invention is illustrated in reference to the following examples, to which the present invention is in no way limited.

In the following, GPC measurement was made using a Waters 2695 HPLC system and Shodex GPC KF-805L columns (three columns directly connected with one another), whereupon 50 μl of a 5 wt % solution of a sample in tetrahydrofuran was poured at a column temperature of 40° C., tetrahydrofuran as an eluant was caused to flow at a rate of 1 ml per minute, and sample peaks were detected on an RI detector (Waters 2414) and a UV detector (Waters 2996). The molecular weights $M_w$, $M_n$ and $M_{Z+1}$ were calculated from the calibration curves as constructed using polystyrene standards.

<Synthesis of Compound I-m>

A mixed solution of 67 g of electronic grade concentrated hydrochloric acid, 305 g of n-butanol, and 133 g of ion-exchanged water was cooled to 10° C., and 59 g of vinyl triethoxysilane was added to the solution dropwise for 15 minutes. Subsequently, the solution was agitated at 25° C. for 18 hours. The precipitated crystals were collected by filtration, and washed with 50 g of electronic grade methanol. The crystals were dissolved in 42 g of tetrahydrofuran, and 42 g of electronic grade methanol and 127 g of ion-exchanged water were sequentially added to the resultant solution with agitation, each in a dropwise manner. The precipitated crystals were collected by filtration, and dried to obtain 4.2 g of the aimed product (compound I-m) as a white solid. The $^1$H-NMR measurement result was as follows. $^1$H-NMR (300 MHz, CDCl$_3$): 6.13-5.88 (m, 24H).

<Synthesis of Compound I-k>

A mixed solution of 136 g of electronic grade concentrated hydrochloric acid, 1 L of n-butanol, and 395 g of ion-exchanged water was cooled to 10° C., and to the solution thus cooled, a mixed solution of 78.3 g of vinyl triethoxysilane and 73.3 g of methyl triethoxysilane was added dropwise for 15 minutes. Subsequently, the mixture was agitated at 25° C. for 18 hours. The precipitated crystals were collected by filtration, and washed with 100 mL of electronic grade methanol. The crystals were dissolved in 500 mL of tetrahydrofuran, and 200 mL of electronic grade methanol and 200 mL of ion-exchanged water were sequentially added to the resultant solution with agitation, each in a dropwise manner. The precipitated crystals were collected by filtration, and dried to obtain 7.8 g of the aimed product (compound I-k) as a white solid. The $^1$H-NMR measurement result was as follows. $^1$H-NMR (300 MHz, CDCl$_3$): 0.28-0.18 (m, 12H), 6.08-5.88 (m, 12H).

Making reference to the above examples of production process, compounds I-a, I-j, and I-r were synthesized. The synthesized compounds are each mentioned before as an example of compound (I).

<Synthesis of Resin A-1>

To 1320 g of electronic grade butyl acetate, 50 g of compound (I-m) was added. The resultant solution was heated to 120° C. in a nitrogen gas flow, and to the solution thus heated, 50.4 ml of the solution which had been prepared by dissolving 0.47 g of a polymerization initiator manufactured by Wako Pure Chemical Industries, Ltd., V-601 (with a ten hour half-life temperature of 66° C.), and 113 mg of 2,6-bis(1,1-dimethylethyl)-4-methyphenol in 235 ml of electronic grade butyl acetate was added dropwise for 80 minutes. After the dropwise addition was terminated, the mixture was agitated at 120° C. for one hour. Subsequently, 3 L of electronic grade methanol and 3 L of ion-exchanged water were added to the reaction solution, and the precipitated solid was collected by filtration, and washed with 100 mL of electronic grade methanol. The solid was dissolved in 724 g of tetrahydrofuran, and 50 g of electronic grade methanol and 150 g of water were sequentially added to the resultant solution with agitation, each in a dropwise manner. After agitation for one hour, the supernatant was discarded by decantation, and 200 g of electronic grade methanol was added. The precipitated solid was collected by filtration, and dried to obtain 17.7 g of the aimed product (resin A-1) as a white solid. The GPC analysis on the resin thus obtained revealed that $M_w=8.7\times10^4$, and $M_n=5.4\times10^4$. The unreacted compound (I-m) comprised not more than 2% by weight of the solid, and no components with a molecular weight of not less than 3,000,000 were observed. When the $^1$H-NMR spectrum was measured using deuterated chloroform as a solvent for measurement, proton peaks (at 0.2 to 3.0 ppm) derived from the alkyl groups which were generated by the polymerization of vinyl groups and proton peaks (at 4.9 to 6.8 ppm) of the remaining vinyl groups were observed at an integral ratio of 2.6/5.4.

<Synthesis of Resin A-2>

To 2878 g of diphenyl ether, 109 g of compound (I-m) was added. The resultant solution was heated to 120° C. in a nitrogen gas flow, and to the solution thus heated, 15.0 ml of the solution which had been prepared by dissolving 168 mg of a polymerization initiator manufactured by Wako Pure Chemical Industries, Ltd., V-601 (with a ten hour half-life temperature of 66° C.), in 74 g of diphenyl ether was added dropwise for 30 minutes. After the dropwise addition was terminated, the mixture was agitated at 120° C. for one hour. Subsequently, 5.4 L of electronic grade methanol and 200 mL of water were added to the reaction solution, and the precipitated solid was collected by filtration, and washed with 200 mL of electronic grade methanol. The solid was dissolved in 1 L of tetrahydrofuran, then 2 L of electronic grade methanol and 125 g of ion-exchanged water were sequentially added to the resultant solution with agitation, and the precipitated solid was collected by filtration, and washed with 200 mL of electronic grade methanol. The above process was repeated two times to obtain after drying 7.26 g of the aimed product (resin A-2) as a white solid. The GPC analysis on the resin thus obtained revealed that $M_w=8.1\times10^4$, and $M_n=4.98\times10^4$. The unreacted compound (I-m) comprised not more than 0.2% by weight of the solid, and no components with a molecular weight of not less than 3,000,000 were observed. When the $^1$H-NMR spectrum was measured using deuterated chloroform as a solvent for measurement, proton peaks (at 0.2 to 3.0 ppm) derived from the alkyl groups which were generated by the polymerization of vinyl groups and proton peaks (at 4.9 to 6.8 ppm) of the remaining vinyl groups were observed at an integral ratio of 2.2/5.8.

<Synthesis of Resin A-3>

To 792 g of diphenyl ether, 30 g of compound (I-m) was added. The resultant solution was heated to 150° C. in a nitrogen gas flow, and to the solution thus heated, 11.4 ml of the solution which had been prepared by dissolving 112 mg of a polymerization initiator manufactured by Wako Pure Chemical Industries, Ltd., VR-110 (azodi-tert-octane with a ten hour half-life temperature of 110° C.), and 22 mg of 2,6-bis(1,1-dimethylethyl)-4-methylphenol in 49.8 g of diphenyl ether was added dropwise for 30 minutes. After the dropwise addition was terminated, the mixture was agitated at 150° C. for one hour. Subsequently, 3.5 L of electronic grade methanol and 150 mL of ion-exchanged water were added to the reaction solution, and the precipitated solid was collected by filtration, and washed with 200 mL of electronic grade methanol. The solid was dissolved in 300 mL of tetrahydrofuran, then 30 mL of electronic grade methanol and 60 mL of ion-exchanged water were sequentially added to the resultant solution with agitation, and the precipitated solid was collected by filtration, and washed with 100 mL of electronic grade methanol. The above process was repeated two times to obtain after drying 12.5 g of the aimed product (resin A-3) as a white solid. The GPC analysis on the resin thus obtained revealed that $M_w=18.3\times10^4$, and $M_n=5.58\times10^4$. The unreacted compound (I-m) comprised not more than 2% by weight of the solid, and no components with a molecular weight of not less than 3,000,000 were observed. When the $^1$H-NMR spectrum was measured using deuterated chloroform as a solvent for measurement, proton peaks (at 0.2 to 3.0 ppm) derived from the alkyl groups which were generated by the polymerization of vinyl groups and proton peaks (at 4.9 to 6.8 ppm) of the remaining vinyl groups were observed at an integral ratio of 1.3/6.7.

<Synthesis of Resin A-4>

To 26.4 g of electronic grade butyl acetate, 1 g of compound (I-m) was added. The resultant solution was heated under reflux at an internal temperature of 127° C., and to the solution as such, the solution which had been prepared by dissolving 1.8 mg of a polymerization initiator manufactured by Wako Pure Chemical Industries, Ltd., V-601 (with a ten hour half-life temperature of 66° C.), in 2 ml of electronic grade butyl acetate was added dropwise for two hours. After the dropwise addition was terminated, the mixture was heated to reflux for another one hour. A polymerization inhibitor, namely 4-methoxyphenol, was added in an amount of 20 mg before the mixture was cooled to room temperature. Subsequently, the mixture was concentrated under vacuum to a liquid weight of 2 g, 20 ml of electronic grade methanol was added to the resultant concentrate, and, after agitation for one hour, the solid was collected by filtration, and dried. The solid was dissolved in 15 ml of tetrahydrofuran, and to the resultant solution, 5 ml of ion-exchanged water was added dropwise with agitation. After agitation for one hour, the supernatant was discarded by decantation, and 10 ml of electronic grade methanol was added. The solid components were collected by filtration, and dried to obtain 0.60 g of the aimed product (resin A-4) as a white solid. The GPC analysis on the resin thus obtained revealed that $M_w$=11.8×10$^4$, $M_n$=3.1×10$^4$, and $M_{Z+1}$=27×10$^4$. The unreacted compound (I-m) comprised not more than 3% by weight of the solid, and no components with a molecular weight of not less than 3,000,000 were observed. When the $^1$H-NMR spectrum was measured for the solid components using deuterated chloroform as a solvent for measurement, proton peaks (at 0.2 to 3.0 ppm) derived from the alkyl groups which were generated by the polymerization of vinyl groups and proton peaks (at 4.9 to 6.8 ppm) of the remaining vinyl groups were observed at an integral ratio of 42/58.

<Synthesis of Resin A-5>

To 13.2 g of electronic grade butyl acetate, 1 g of compound (I-m) was added. The resultant solution was heated under reflux at an internal temperature of 127° C., and to the solution as such, the solution which had been prepared by dissolving 1 mg of a polymerization initiator manufactured by Wako Pure Chemical Industries, Ltd., V-40 (with a ten hour half-life temperature of 88° C.), in 1 ml of electronic grade butyl acetate was added dropwise for four hours. After the dropwise addition was terminated, the mixture was heated to reflux for another one hour. A polymerization inhibitor, namely 4-methoxyphenol, was added in an amount of 20 mg before the mixture was cooled to room temperature. Subsequently, the mixture was concentrated under vacuum to a liquid weight of 2 g, 20 ml of electronic grade methanol was added to the resultant concentrate, and, after agitation for one hour, the solid was collected by filtration, and dried. The solid was dissolved in 10 ml of tetrahydrofuran, and to the resultant solution, 1.8 ml of ion-exchanged water was added dropwise with agitation. After agitation for one hour, the supernatant was discarded by decantation, and 10 ml of electronic grade methanol was added. The solid components were collected by filtration, and dried to obtain 0.41 g of the aimed product (resin A-5) as a white solid. The GPC analysis on the resin thus obtained revealed that $M_w$=12.8×10$^4$, $M_n$=3.3×10$^4$, and $M_{Z+1}$=38×10$^4$. The unreacted compound (I-m) comprised not more than 3% by weight of the solid, and no components with a molecular weight of not less than 3,000,000 were observed. When the $^1$H-NMR spectrum was measured for the solid components using deuterated chloroform as a solvent for measurement, proton peaks (at 0.2 to 3.0 ppm) derived from the alkyl groups which were generated by the polymerization of vinyl groups and proton peaks (at 4.9 to 6.8 ppm) of the remaining vinyl groups were observed at an integral ratio of 53/47.

Making reference to the above examples of production process, resins A-6 through A-11 were synthesized. The type and the compositional ratio of compounds (I) as used for the synthesis of individual resins, as well as the weight-average molecular weight and the number-average molecular weight of the synthesized resins are set forth in Table 1.

<Synthesis of Resin X-1>

To 4 g of diphenyl ether, 800 mg of resin (A-1), 50 mg of 2,6-bis(1,1-dimthylethyl)-4-methylphenol, and 8 g of dicyclopentadiene were added.

The resultant solution was heated to 180° C. in a nitrogen gas flow, and agitated for three hours. After the agitation, the reaction solution was added to 200 ml of electronic grade methanol, and the precipitated solid was collected by filtration, and dried to obtain, as a white solid, 820 mg of the aimed product (resin X-1) which had the Diels-Alder adduct moiety as represented by general formula (F-2). The GPC analysis on the resin thus obtained revealed that $M_w$=11.5×10$^4$, and $M_n$=5.29×10$^4$. Neither the unreacted cyclopentadiene nor a component with a molecular weight of not less than 3,000, 000 was observed in the solid. When the $^1$H-NMR spectrum was measured for the solid components using deuterated chloroform as a solvent for measurement, proton peaks (at 0.2 to 3.0 ppm) derived from the alkyl groups which were generated by the polymerization of vinyl groups and the alkyl groups which were generated by Diels-Alder reaction, and proton peaks (at 4.9 to 6.8 ppm) derived from the remaining vinyl groups and the olefins which were generated by Diels-Alder reaction were observed at an integral ratio of 30:70. During the thermogravimetric analysis (on an instrument SDT Q600 of TA Instruments, Inc.; the nitrogen flow rate, 100 ml/min; the rate of temperature rise, 20° C./min), a 28% reduction in weight was observed at 340° C., which thus confirmed the addition amount (% by weight) of cyclopentadiene in resin X-1.

<Synthesis of Resin X-2>

To 4 g of diphenyl ether, 800 mg of resin (A-2), 50 mg of 2,6-bis(1,1-dimthylethyl)-4-methylphenol, and 800 mg of pentamethyl cyclopentadiene were added. The resultant solution was heated to 180° C. in a nitrogen gas flow, and agitated for three hours. The reaction solution was added to 200 ml of electronic grade methanol, and the precipitated solid was collected by filtration, and dried to obtain, as a white solid, 910 mg of the aimed product (resin X-2) which had the Diels-Alder adduct moiety as represented by general formula (F-2). The GPC analysis on the resin thus obtained revealed that $M_w$=9.47×10$^4$, and $M_n$=5.86×10$^4$. Neither the unreacted pentamethyl cyclopentadiene nor a component with a molecular weight of not less than 3,000,000 was observed in the solid. When the $^1$H-NMR spectrum was measured for the solid components using deuterated chloroform as a solvent for measurement, proton peaks (at 0.2 to 3.0 ppm) derived from the alkyl groups which were generated by the polymerization of vinyl groups and the alkyl groups which were generated by Diels-Alder reaction, and proton peaks (at 4.9 to 6.8 ppm) derived from the remaining vinyl groups and the olefins which were generated by Diels-Alder reaction were observed at an integral ratio of 85:15. During the thermogravimetric analysis (on an instrument SDT Q600 of TA Instruments, Inc.; the nitrogen flow rate, 100 ml/min; the rate of temperature rise, 20° C./min), a 44% reduction in weight was observed at 336° C., which thus confirmed the addition amount (% by weight) of pentamethyl cyclopentadiene in resin X-2.

<Synthesis of Resin X-3>

To 4 g of diphenyl ether, 800 mg of resin (A-2), 50 mg of 2,6-bis(1,1-dimethylethyl)-4-methylphenol, and 240 mg of pentamethyl cyclopentadiene were added. The resultant solution was heated to 180° C. in a nitrogen gas flow, and agitated for three hours. The reaction solution was added to 200 ml of electronic grade methanol, and the precipitated solid was collected by filtration, and dried to obtain, as a white solid, 910 mg of the aimed product (resin X-3) which had the Diels-Alder adduct moiety as represented by general formula (F-2). The GPC analysis on the resin thus obtained revealed that $M_w=10.6\times10^4$, and $M_n=5.49\times10^4$. Neither the unreacted pentamethyl cyclopentadiene nor a component with a molecular weight of not less than 3,000,000 was observed in the solid. When the $^1$H-NMR spectrum was measured for the solid components using deuterated chloroform as a solvent for measurement, proton peaks (at 0.2 to 3.0 ppm) derived from the alkyl groups which were generated by the polymerization of vinyl groups and the alkyl groups which were generated by Diels-Alder reaction, and proton peaks (at 4.9 to 6.8 ppm) derived from the remaining vinyl groups and the olefins which were generated by Diels-Alder reaction were observed at an integral ratio of 60:40. During the thermogravimetric analysis (on an instrument SDT Q600 of TA Instruments, Inc.; the nitrogen flow rate, 100 ml/min; the rate of temperature rise, 20° C./min), a 14% reduction in weight was observed at 330° C., which thus confirmed the addition amount (% by weight) of pentamethyl cyclopentadiene in resin X-3.

Making reference to the above examples of production process, resins X-4 through X-12 were synthesized. The type of resins A and the diene compounds as used for the synthesis of individual resins, as well as the weight-average molecular weight and the number-average molecular weight of the synthesized resins are set forth in Table 1.

In Table 1, the addition amount of diene B is set forth as the amount (in % by weight) of diene B in resin X.

TABLE 1

| | Resin X $M_w/M_n(\times10^4)$ | Diene B (addition amount, wt %) | Resin A | $M_w/M_n(\times10^4)$ | Repeating unit | Compositional ratio (by weight) | Solvent for polymerization, and temperature |
|---|---|---|---|---|---|---|---|
| X-1 | 11.5/5.29 | Cyclopentadiene (28 wt %) | A-1 | 8.7/5.4 | I-m | 100 | Butyl acetate, 120° C. |
| X-2 | 9.47/5.86 | pentamethyl cyclopentadiene (44 wt %) | A-2 | 8.1/4.98 | I-m | 100 | Diphenyl ether, 120° C. |
| X-3 | 10.6/5.49 | pentamethyl cyclopentadiene (14 wt %) | A-2 | 8.1/4.98 | I-m | 100 | Diphenyl ether, 120° C. |
| X-4 | 19.8/9.2 | Cyclopentadiene (41 wt %) | A-3 | 18.3/5.58 | I-m | 100 | Diphenyl ether, 120° C. |
| X-5 | 16.7/4.2 | Cyclopentadiene (11wt %) | A-4 | 11.8/3.1 | I-m | 100 | Butyl acetate, 120° C. |
| X-6 | 14.3/5.5 | Cyclopentadiene (35 wt %) | A-5 | 12.8/3.3 | I-m | 100 | Butyl acetate, 120° C. |
| X-7 | 11.1/5.92 | Cyclopentadiene (14 wt %) | A-6 | 9.78/5.6 | I-k | 100 | Butyl acetate, 120° C. |
| X-8 | 40.8/20.6 | pentamethyl cyclopentadiene (32 wt %) | A-7 | 32.1/16.9 | I-k | 100 | Propylene glycol monomethyl ether acetate, 120° C. |
| X-9 | 11.9/6.12 | pentamethyl cyclopentadiene (26 wt %) | A-8 | 9.78/5.6 | I-m/I-k | 50/50 | Butyl acetate, 120° C. |
| X-10 | 5.21/2.63 | α-phellandrene (10 wt %) | A-9 | 2.56/1.22 | I-a | 100 | t-Butylbenzene, 130° C. |
| X-11 | 21.3/12.6 | α-terpinene (19 wt %) | A-10 | 16.3/7.62 | I-m/I-k/I-r | 30/40/30 | Butyl acetate, 120° C. |
| X-12 | 5.51/3.22 | Cyclopentadiene (6 wt %) | A-11 | 4.56/2.51 | I-j/I-r | 70/20 | Cyclohexanone, 60° C. |

Making reference to the above production processes for resins A-1 through A-5, and using compounds (I-s) through (I-z) and (I-aa) each exemplifying compound (X) as described before, polymerization was carried out under the conditions for polymerization (solvent, temperature) as set forth in Table 2. The weight-average molecular weight and the number-average molecular weight of the polymers as produced by polymerization reaction are set forth in Table 2.

The exemplary compounds (I-s) through (I-z) and (I-aa) were synthesized making reference to the production processes for the exemplary compound (I-k) and so forth as described above, and the synthesis method of JP 2008-210970 A.

TABLE 2

| Resin X | Mw/Mn (×10⁴) | Repeating unit | Compositional ratio (by weight) | Solvent for polymerization, and temperature |
|---|---|---|---|---|
| X-13 | 5.07/3.60 | I-s | 100 | Cyclohexanone, 120° C. |
| X-14 | 10.1/3.6 | I-t | 100 | Butyl acetate, 120° C. |
| X-15 | 15.3/5.9 | I-u | 100 | Butyl acetate, 120° C. |
| X-16 | 0.93/0.32 | I-v | 100 | Cyclohexanone, 140° C. |
| X-17 | 0.63/0.22 | I-w | 100 | Butyl acetate, 120° C. |
| X-18 | 4.52/2.69 | I-x | 100 | Diphenyl ether, 120° C. |
| X-19 | 5.01/0.90 | I-y | 100 | Propylene glycol monomethyl ether acetate, 120° C. |
| X-20 | 12.6/4.3 | I-z | 100 | Tetrahydrofuran, 60° C. |
| X-21 | 1.12/0.35 | I-u | 100 | Cyclohexanone, 120° C. |
| X-22 | 8.71/4.23 | I-aa | 100 | Cyclohexanone, 120° C. |

<Synthesis of Resin H-1>

Following the method as described in JP 2007-161788 A, a polymer of 1,3-diethynyl adamantane was synthesized as polymer (G-1). The GPC analysis on the polymer thus obtained revealed that $M_w=1.37\times10^4$, and $M_n=0.39\times10^4$.

Polymer (G-1), 12.9 g in amount, was dissolved in 30 mL of toluene, and 175 mL of DIBAL-H (1 M solution in hexane) was added to the resultant toluene solution as kept cooled to 0° C. The solution was then agitated at room temperature for three hours. A saturated aqueous solution of ammonium chloride, 230 mL in amount, was cooled, and the reaction solution was added to the cooled solution. The mixture was filtrated, and the filtrate was extracted from ethyl acetate. The organic layer was dried over sodium sulfate, then the solution was concentrated under vacuum. The crude product thus obtained was dissolved in a small amount of tetrahydrofuran, the resultant solution was added to 300 mL of methanol, and the precipitated solid was collected by filtration, and dried to obtain 10.3 g of the aimed product (resin H-1) as a white solid.

The GPC analysis on the resin thus obtained revealed that $M_w=1.35\times10^4$, and $M_n=0.39\times10^4$.

[Chemical Formula 19]

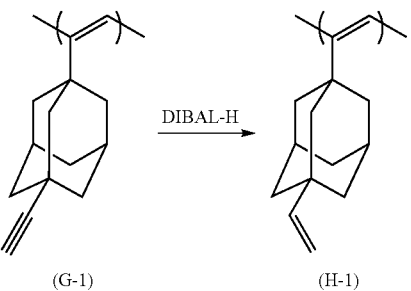

<Synthesis of Resin H-2>

Following the method as described in JP 2007-161786 A, a polymer of 4,9-diethynyl diamantane was synthesized as polymer (G-2). The GPC analysis on the polymer thus obtained revealed that $M_w=1.66\times10^4$, and $M_n=0.54\times10^4$.

Resin (H-2) was obtained by following the synthesis procedure for resin (H-1) except that polymer (G-2) was used instead of polymer (G-1). The GPC analysis on the resin thus obtained revealed that $M_w=1.65\times10^4$, and $M_n=0.51\times10^4$.

[Chemical Formula 20]

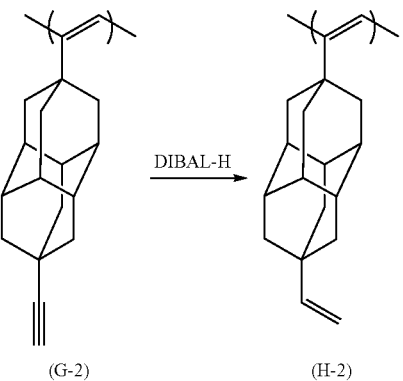

<Synthesis of Resin H-3>

Pursuant to the method as described in JP 2003-520864 A, a vinyl-containing polyarylene ether (resin H-3) was synthesized.

[Chemical Formula 21]

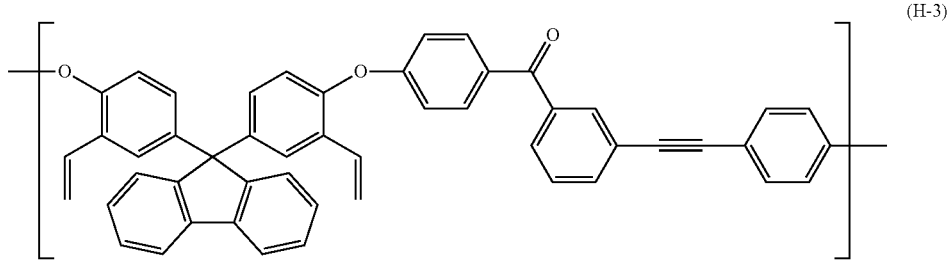

<Synthesis of Compound H-4>

Compound G-4 was synthesized by following the tetrakis (tolanyl)adamantane synthesizing method as described in JP 2004-504455 A except that phenylacetylene was replaced by a mixture of phenylacetylene and (trimethylsilyl)acetylene (in equimolar amounts). Subsequently, a (trimethylsilyl)ethynyl group was converted into a vinyl group according to the method as described in JP 2007-314778 A so as to obtain compound H-4.

In the formulae as below, $R^1$ is a mixture of a phenyl group and a trimethylsilyl group, and $R^2$ is a mixture of a phenylethynyl group and a vinyl group.

[Chemical Formula 22]

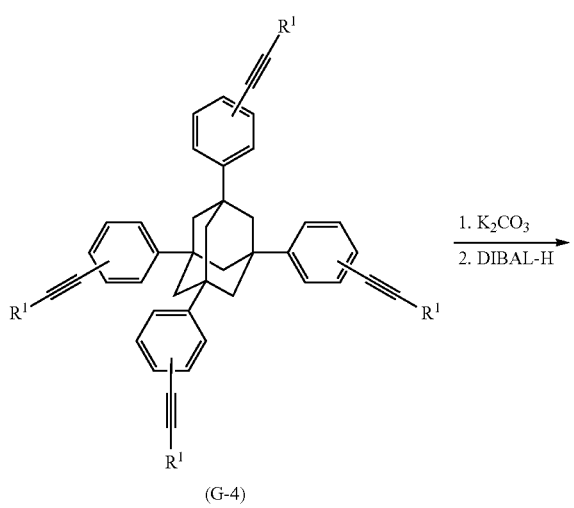

(G-4)

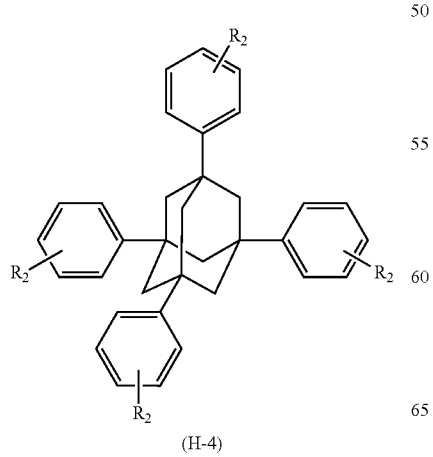

(H-4)

<Synthesis of Resin H-5>

Pursuant to the method as described in WO 2005/019305, a vinyl-containing polybenzoxazole (resin H-5) was synthesized.

[Chemical Formula 23]

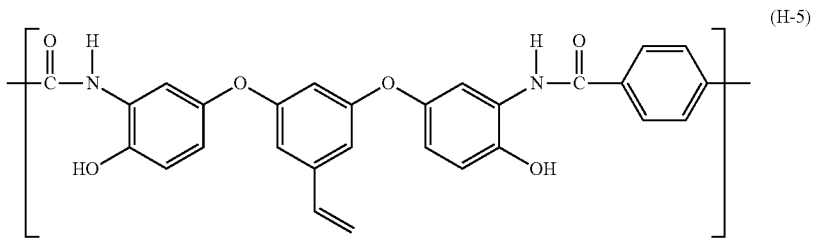

Making reference to the exemplary production processes for resins X-1 through X-3 and using resins H-1 through H-5, resins X-23 through X-28 were synthesized. The type of resins H and the diene compounds as used for the synthesis of individual resins, as well as the weight-average molecular weight and the number-average molecular weight of the synthesized resins are set forth in Table 3.

In Table 3, the addition amount of diene B is set forth as the amount (in % by weight) of diene B in resin X.

TABLE 3

| Resin X | | Diene B | |
|---|---|---|---|
| | Mw/Mn(×10⁴) | (addition amount, wt %) | Resin H |
| X-23 | 2.3/0.9 | Cyclopentadiene (40 wt %) | H-1 |
| X-24 | 3.9/1.2 | Cyclopentadiene (35 wt %) | H-2 |
| X-25 | 8.56/2.33 | Cyclopentadiene (40 wt %) | H-2 |
| X-26 | 0.90/0.31 | Cyclopentadiene (8 wt %) | H-3 |
| X-27 | 1.56/0.74 | Cyclopentadiene (20 wt %) | H-4 |
| X-28 | 1.36/0.34 | Cyclopentadiene(15 wt %) | H-5 |

<Preparation of Composition>

The resins obtained as described above were dissolved in the solvents as set forth in Table 4 below to prepare solutions each having a solid component concentration of 8% by weight. The solutions were each filtrated through a 0.1 μm tetrafluoroethylene filter, and applied onto a 4-inch silicon wafer by a spin coating technique. The substrates were subjected to predrying on a hot plate at 110° C. for one minute, then at 200° C. for one minute, so as to form coating films each having a thickness of 400 nm.

The coating films thus obtained were cured by one out of the following methods.

(1) Heating

Heating was performed in a nitrogen atmosphere in a clean oven CLH-21 CD (III) manufactured by Koyo Thermo Systems Co., Ltd. at 400° C. for 60 minutes.

(2) EB Irradiation

Using an irradiating system Min-EB manufactured by USHIO INC., irradiation with an electron beam at a dose of 1 μCcm$^{-2}$ was performed in an Ar atmosphere for five minutes under such conditions that the pressure was 100 kPa, the substrate temperature was 350° C., and the electron accelerating voltage was 20 keV.

(3) UV Irradiation

Using a dielectric barrier discharge excimer lamp UER20-172 manufactured by USHIO INC., irradiation with 172-nm light at an energy amount of 100 mJ/cm² was performed on a hot plate at 350° C. in a nitrogen gas flow for five minutes.

The cured films were evaluated as described later. The results are set forth in Table 4.

In Table 4, the surfactant content is set forth in % by weight on the total amount of each composition (coating solution). On the other hand, the adhesion promoter content is set forth in % by weight on the total solid components in each composition (coating solution).

TABLE 4

| | Resin | Solvent | Surfactant (0.01 wt %) | Adhesion promoter (0.05 wt %) | Curing method | Relative dielectric constant | Young's modulus of elasticity (MPa) | Long-lasting stability of relative dielectric constant |
|---|---|---|---|---|---|---|---|---|
| Ex. 1 | X-1 | Cyclohexanone | — | — | Heating | 1.99 | 4.5 | ○ |
| Ex. 2 | X-2 | Cyclohexanone | — | — | EB irradiation | 2.04 | 5 | ○ |
| Ex. 3 | X-3 | Cyclohexanone | — | — | EB irradiation | 2.1 | 5.1 | ○ |
| Ex. 4 | X-4 | Cyclohexanone | — | — | EB irradiation | 2.01 | 4.9 | ○ |
| Ex. 5 | X-5 | Cyclohexanone | — | — | Heating | 2.12 | 5.3 | ○ |
| Ex. 6 | X-6 | Propylene glycol monomethyl ether acetate | — | — | EB irradiation | 2.05 | 5.5 | ○ |
| Ex. 7 | X-7 | Propylene glycol monomethyl ether acetate | — | — | EB irradiation | 2.15 | 4.8 | ○ |
| Ex. 8 | X-8 | Propylene glycol monomethyl ether | BYK-307 | — | EB irradiation | 2.11 | 4.9 | ○ |
| Ex. 9 | X-9 | Propylene glycol monomethyl ether acetate | — | — | EB irradiation | 2.01 | 5.6 | ○ |
| Ex. 10 | X-10 | Cyclohexanone | — | — | UV irradiation | 1.94 | 6.1 | ○ |
| Ex. 11 | X-11 | Cyclohexanone | — | — | EB irradiation | 2.09 | 4.3 | ○ |
| Ex. 12 | X-12 | Propylene glycol monomethyl ether acetate | — | 3-Glycidyl-oxypropyl trimethoxy-silane | EB irradiation | 2.2 | 7.1 | ○ |
| Comp. Ex. 1 | A-1 | Cyclohexanone | — | — | Heating | 2.43 | 3.1 | X |
| Comp. Ex. 2 | A-2 | Propylene glycol monomethyl ether acetate | — | — | Heating | 2.62 | 2.9 | X |
| Ex. 13 | X-13 | Butyl acetate | — | — | UV irradiation | 2.25 | 5.63 | ○ |
| Ex. 14 | X-14 | Propylene glycol monomethyl ether acetate | — | — | Heating | 2.06 | 5.12 | ○ |
| Ex. 15 | X-15 | Propylene glycol monomethyl ether acetate | — | — | EB irradiation | 2.04 | 5.19 | ○ |
| Ex. 16 | X-16 | Cyclohexanone | — | — | EB irradiation | 1.96 | 4.51 | ○ |
| Ex. 17 | X-17 | Cyclohexanone | — | — | Heating | 2.12 | 5.32 | ○ |
| Ex. 18 | X-18 | Cyclohexanone | — | — | EB irradiation | 2.11 | 5.53 | ○ |
| Ex. 19 | X-19 | Cyclohexanone | — | — | EB irradiation | 1.92 | 4.87 | ○ |
| Ex. 20 | X-20 | Cyclohexanone | — | — | Heating | 1.96 | 4.78 | ○ |
| Ex. 21 | X-21 | Cyclohexanone | — | — | EB irradiation | 2.24 | 6.21 | ○ |
| Ex. 22 | X-22 | Butyl acetate | — | — | Heating | 2.26 | 6.13 | ○ |
| Ex. 23 | X-23 | Cyclohexanone | — | — | EB irradiation | 2.29 | 5.78 | ○ |
| Ex. 24 | X-24 | Cyclohexanone | — | — | EB irradiation | 2.21 | 5.51 | ○ |
| Ex. 25 | X-25 | Tetrahydrofuran | — | — | Heating | 2.29 | 5.23 | ○ |
| Ex. 26 | X-26 | Tetrahydrofuran | — | — | Heating | 2.30 | 5.13 | ○ |
| Ex. 27 | X-27 | Tetrahydrofuran | — | — | EB irradiation | 2.31 | 4.95 | ○ |
| Ex. 28 | X-28 | Tetrahydrofuran | — | — | EB irradiation | 2.22 | 6.35 | ○ |

<Relative Dielectric Constant>

Using a mercury probe manufactured by Four Dimensions, Inc. and an LCR meter HP 4285 A manufactured by Yokogawa-Hewlett-Packard Company, the relative dielectric constant was calculated from a capacity value at 1 MHz (measured at a temperature of 25° C.).

<Young's Modulus of Elasticity>

The Young's modulus of elasticity was measured using a nanoindenter SA2 manufactured by MTS Systems Corporation.

<Long-Lasting Stability of Relative Dielectric Constant>

The wafers as obtained were left standing in an atmosphere at 23° C. and 40% RH (relative humidity) for four weeks before the relative dielectric constant was determined again by the method as described above. A variation in relative dielectric constant falling within the range of ±0.1 is denoted by the symbol "O" and a variation not falling the range by the symbol "X."

<Evaluation on Heat Resistance after Film Formation>

Evaluation on heat resistance was conducted by heating the obtained films in the air at 400° C. for 60 seconds, then measuring them in rate of change in thickness. The coating film whose rate of change in thickness is nearer to zero in value is considered to be more resistant to heat. While the films of Examples 1 and 2 had rates of change in thickness of 6.8% and 4.8%, respectively, the films of Comparative Examples 1 and 2 had rates of 10.1% and 8.9%, respectively.

It was confirmed from the results as set forth in Table 4 that the film which is low in relative dielectric constant, excellent in long-lasting stability of the relative dielectric constant and in heat resistance, as well as high in Young's modulus of elasticity is attained through curing by various techniques including heating, EB irradiation, and UV irradiation if the composition for film formation of the present invention is used.

In contrast, the films as obtained in Comparative Examples 1 and 2 in each of which the diene compound was not released during curing treatment were both high in relative dielectric constant and low in Young's modulus of elasticity. In addition, they were inferior in long-lasting stability of the relative dielectric constant, and in heat resistance as well.

Example 29

In a 50 ml three-neck flask, 2.79 g of bicyclo[2.2.1]hept-5-en-2-yl trimethoxysilane (of the formula as below), 625 mg of tetraethoxysilane, 2.32 g of methyl triethoxysilane, 100 mg of oxalic acid, 12 ml of isopropyl alcohol, 8 ml of butanol, and 3 ml of ion-exchanged water were placed, and heated under reflux for seven hours. After being left to cool, the mixture was filtrated through a 0.1 μm tetrafluoroethylene filter.

The composition thus obtained was applied onto a 4-inch silicon wafer by a spin coating technique. The substrate was subjected to drying on a hot plate at 80° C. for five minutes, then at 200° C. for five minutes and baking in a nitrogen atmosphere in an oven at 400° C. for 60 minutes so as to form a film with a thickness of 400 nm.

When the film as obtained was measured similarly to the above films, it had a relative dielectric constant of 2.1, a Young's modulus of elasticity of 5.4 MPa, and a long-lasting stability of the relative dielectric constant denoted by "O."

[Chemical Formula 24]

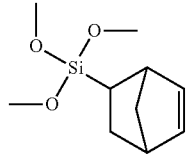

<Pore Diameter Measurement>

From each cured film accompanied by the wafer on which it was formed, a 2.0 cm×0.5 cm rectangular specimen was cut, and placed in a cell for gas adsorption measurement to conduct nitrogen gas adsorption measurement using a pore distribution and specific surface area measuring instrument Autosorb-1 manufactured by Quantachrome Instruments. The data from the measurement were analyzed by an N2/DFT method (N2 at 77K on silica (cylindrical pore, NLDFT equilibrium model)) and, with respect to the pore distribution (distribution of pores in the relevant film specimen) thus determined, the diameter of highest frequency (at which the maximum peak appeared) was assumed as the maximum distributed diameter.

The diameter of highest frequency was 2.5 nm, 2.8 nm and 1.9 nm in Examples 1, 2 and 17, respectively, while 7.8 nm and 9.2 nm in Comparative Examples 1 and 2, respectively.

The invention claimed is:

1. A composition comprising compound (X) having a functional group, wherein the functional group is partially eliminated by heating, irradiation with light, irradiation with radiation, or a combination thereof, so that it generates a volatile component, and yields an unsaturated group in a remaining part, and further wherein:

said compound (X) is a compound which has a Diels-Alder adduct moiety produced by Diels-Alder reaction between a conjugated diene structure and a dienophile structure, and generating the conjugated diene structure and the dienophile structure upon retro-Diels-Alder reaction caused by heating, irradiation with light, irradiation with radiation, or a combination thereof, and also has a siloxane structure, said compound (X) is a compound which is produced by Diels-Alder reaction between compound (A) having a dienophile structure and a siloxane structure as well and compound (B) having a conjugated diene structure, and releases the compound (B) having a conjugated diene structure through retro-Diels-Alder reaction caused by heating, irradiation with light, irradiation with radiation, or a combination thereof, and said compound (A) is a polymer having compound (I) as a repeating unit, and the compound (I) has m number of $RSi(O_{0.5})_3$ units where m is an integer of 8 to 16, and each R is independently a hydrogen atom or a substituent, with the units sharing oxygen atoms therein to link to one another and thereby forming a cage structure, and wherein the compound (I)-derived components comprise not less than 70% by weight of the polymer.

2. The composition according to claim 1, wherein said compound (I) is a compound represented by one out of general formulae (Q-1) through (Q-7):

Chemical Formula 1

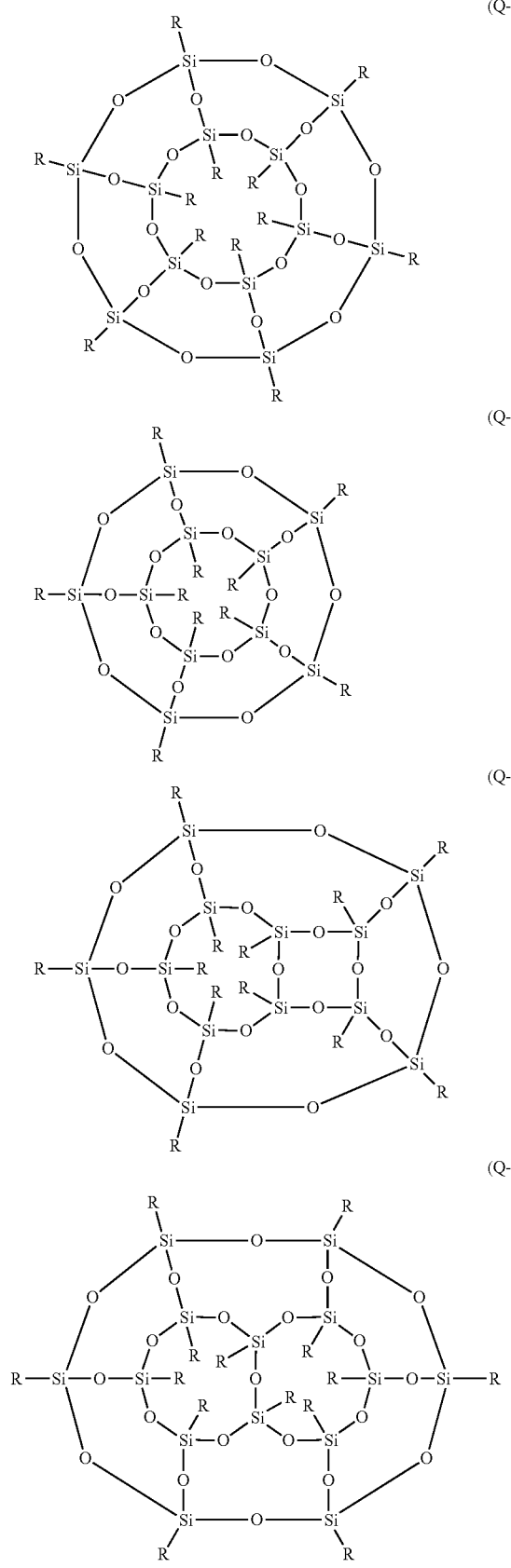

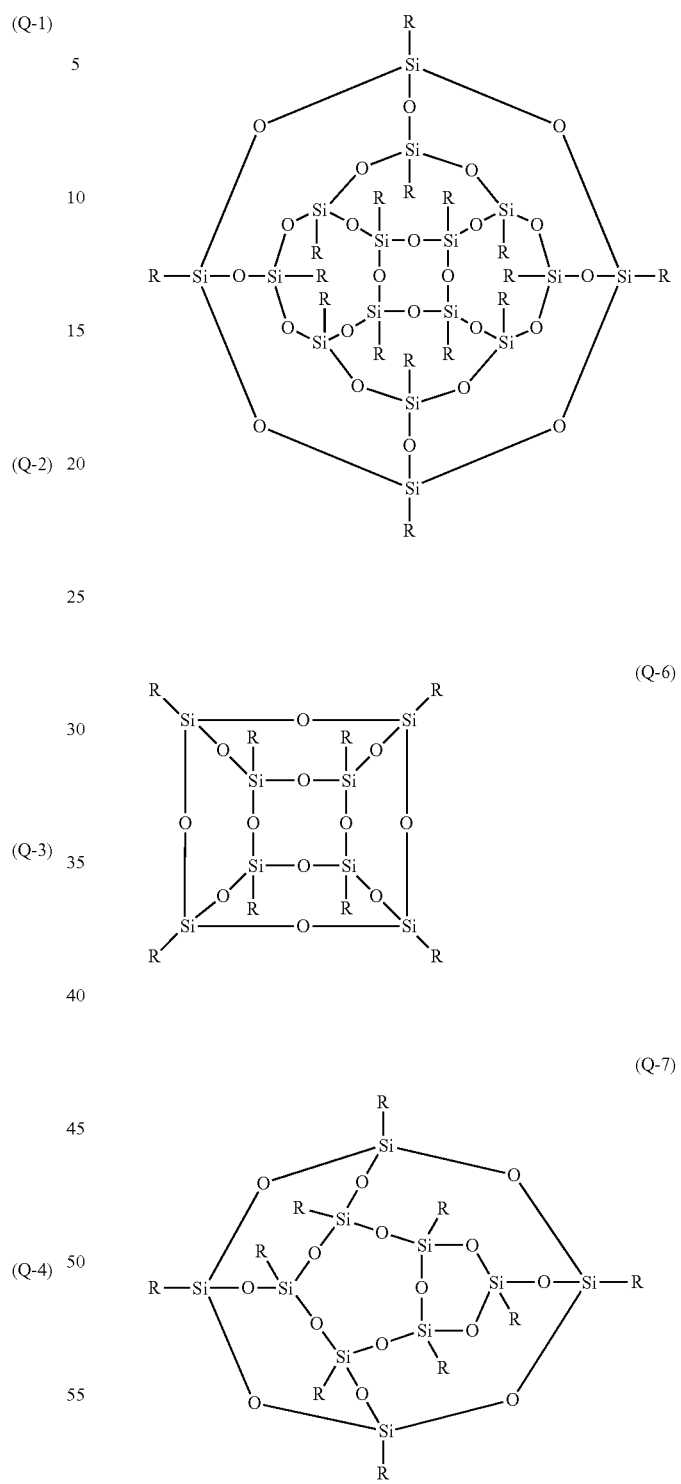

wherein in general formulae (Q-1) through (Q-7), each R is independently a hydrogen atom or a substituent; and in each of general formulae (Q-1) through (Q-7), at least one R is an alkenyl group or an alkynyl group.

3. The composition according to claim 1, wherein said compound (B) having a conjugated diene structure is a compound represented by one out of general formulae (B-1) through (B-3):

Chemical Formula 2

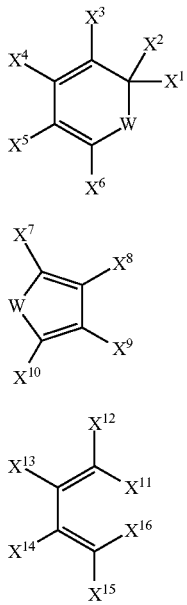

General formula (B-1)

General formula (B-2)

General formula (B-3)

wherein in general formulae (B-1) through (B-3), $X^1$ to $X^{16}$ are each independently a hydrogen atom or a substituent; and in general formulae (B-1) and (B-2), W is —O—, —C(O)—, —C(O)O—, —S(O)—, —S(O)$_2$—, —C($X^{17}$)($X^{18}$)—, or —N($X^{19}$)—, with $X^{17}$ to $X^{19}$ being each independently a hydrogen atom or a substituent.

4. The composition according to claim 1, wherein the addition amount of said compound (B) in said compound (X) is 5 to 80% by weight based on the total amount of the compound (X).

5. The composition according to claim 1, further comprising a solvent.

6. A method of fabricating an insulator film, comprising applying the composition according to claim 1 onto a substrate, and curing a film formed of the composition as applied.

7. The composition according to claim 2, wherein said compound (B) having a conjugated diene structure is a compound represented by one out of general formulae (B-1) through (B-3):

Chemical Formula 6

General formula (B-1)

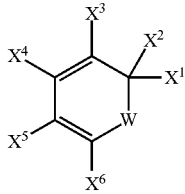

General formula (B-2)

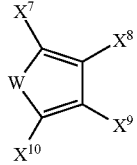

General formula (B-3)

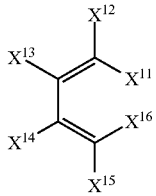

wherein in general formulae (B-1) through (B-3), $X^1$ to $X^{16}$ are each independently a hydrogen atom or a substituent; and in general formulae (B-1) and (B-2), W is —O—, —C(O)—, —C(O)O—, —S(O)—, —S(O)$_2$—, —C($X^{17}$)($X^{18}$)—, or —N($X^{19}$)—, with $X^{17}$ to $X^{19}$ being each independently a hydrogen atom or a substituent.

8. The composition according to claim 2, wherein the addition amount of said compound (B) in said compound (X) is 5 to 80% by weight based on the total amount of the compound (X).

* * * * *